United States Patent [19]
Van de Capelle et al.

[11] Patent Number: 5,933,578
[45] Date of Patent: Aug. 3, 1999

[54] METHOD AND DEVICE FOR DETERMINING THE COLOR APPEARANCE OF COLOR OVERPRINTS

[75] Inventors: Jean-Pierre Van de Capelle, Merelbeke; Baldewin Meireson, Zingem, both of Belgium

[73] Assignee: Barco Graphics, N.V., Belgium

[21] Appl. No.: 08/824,689

[22] Filed: Apr. 8, 1997

[51] Int. Cl.$^6$ .............................. G06F 15/00; B41F 19/02; G03C 7/00

[52] U.S. Cl. ............................ 395/109; 101/23; 345/431; 430/358; 430/359

[58] Field of Search ............................ 395/109; 358/500, 358/501, 504, 518, 525, 534; 345/431; 430/21, 42, 43, 357, 358, 359, 362; 101/23

[56] References Cited

U.S. PATENT DOCUMENTS

| | | | |
|---|---|---|---|
| 5,428,720 | 6/1995 | Adams, Jr. ............................... | 395/131 |
| 5,596,425 | 1/1997 | Usui, et al. ............................. | 358/500 |

FOREIGN PATENT DOCUMENTS

| | | | |
|---|---|---|---|
| 0613062A | 8/1994 | European Pat. Off. ....... | G03G 15/01 |
| 0763928A | 3/1997 | European Pat. Off. ......... | H04N 1/60 |

OTHER PUBLICATIONS

PCT search report for PCT Application number PCT/BE98/00050 (mailed Aug. 8, 1998).

"Usage of the Chameleon Accelerator for Color Transformations" by J. P. Van de Capelle and L. Plettinck, *Proceedings of the second IS&T/SID Color Imaging conference on Color Science, Systems and Applications*, pp. 165–166, Nov. 1994.

"Kubelka–Munk Theory and the Prediction of Reflectance," by James H. Nobbs, *Rev. Prog. Coloration*, vol. 15, pp. 66–75, 1985.

"Predicting the Spectral Behavior of Colour Printers for Transparent Inks on Transparent Support," by P. Emmel, I. Amidror, V. Ostromoukhov, and R.J. Hersch, *Proceedings of the Fourth IS&T/SID Color Imaging Conference on Color Science, Systems and Applications*, pp. 86–91, Nov. 1996.

*Primary Examiner*—Edward L. Coles
*Assistant Examiner*—Mark Wallerson
*Attorney, Agent, or Firm*—Don Rosenfeld

[57] ABSTRACT

A method and apparatus for determining a small number of parameters that spectrally characterize colorants by a small number of parameters and for using such colorant parameters to predict the spectral reflection or transmission characteristics of such colorants when laid on top of one another, either on an opaque, transparent or semitransparent carrier of a particular type, each colorant laid with a certain coverage percentage, for example, dot percentage in the case of offset printing, the colorant parameters of any colorant being substantially independent of the color of the substrate. The method involves making measurements of sets prints of varying coverage percentages of a colorant on a number of backgrounds, and solving the resulting set of equations for the colorant. Colorants that are defined by a recipe of basic colorants can be characterized from measurements on prints of the basic colorants.

50 Claims, 7 Drawing Sheets

METHOD AND DEVICE FOR DETERMINING THE COLOR APPEARANCE OF COLOR OVERPRINTS

FIELD OF THE INVENTION

The present invention relates to computerized color graphics, color reproduction, and electronic printing systems. In particular, the present invention relates to a method and apparatus for characterizing colorants and predicting the color appearance of placing one or more colorant layers on top of a substrate such as paper or film as occurs, for example, in printing a page or in photography.

BACKGROUND OF THE INVENTION

Computerized color graphics systems and electronic printing systems are known in the art. Typically, they enable a user to produce a color image, and from that image to produce a picture which can be printed via a color reproduction system, for example, by producing color separation plates for offset printing. There has been much effort in the past to develop ways to accurately predict the appearance of such images when printed on a substrate, for example paper or film, using a number of colorants, such as inks, the prediction carried out without actually printing the images. It should be noted that an image in the context of the present invention, may include text, graphic line art, continuous tone images, and/or any visual two-dimensional pattern.

Often, printing is carried out using halftoning. Halftoning, also called screening, is the process of creating the illusion of a continuous tone ("CT," "contone") image using an output (e.g., printing) device capable only of binary output (ink deposited or not deposited at any location on a substrate). Halftoning involves the placement of binary (ink or no ink) picture elements, and the amount of ink picture elements placed per unit area ("dot percentage") determines the tone. For color printing, several images ("separations") are produced in the primary colorants (typically inks) used to print in color, and overlaid in printing. For typical four color printing, four images are produced in cyan ("C"), magenta ("M"), yellow ("Y") and black ("K"), and each of these images are halftoned. Halftoning is also called screening because historically in pre-electronic days, a physical screen was used. If a halftone pattern is regular, the individual halftone cells are called "screen dots" and they are said to be part of a "screen." Usually, digital halftoning is used together with an imagesetter, laser printer, ink jet printer, digital film recorder, or other recorder output device. Each of these devices has a fundamental recording element, herein called a pixel, which represents an element on which ink can be deposited, or not. This smallest unit on a recorder is called a "microdot," "recorder element," "recorder pixel," or the like. Its size is called the "recorder pitch," "recorder resolution," "imagesetter resolution," etc., and is expressed either as units of recorder element size, e.g, $1/1800$ of an inch, or a spatial frequency, e.g., 1800 pixels per inch (ppi) or 1800 dots per inch (dpi). Some presses nowadays have pixels which can have intermediate levels between on and off. This is for instance obtained by the amount of colorant (typically ink) deposited on that pixel. For example, in a four level printer, there can be 0%, 33%, 67% or 100% of the maximum amount of ink applied on any one pixel element. It is then said for such a printer that a pixel has a 2-bit value, instead of a 1-bit value.

It is desirable to be able to calculate very accurately how a picture will look when one prints an image, including a halftoned continuous tone color image, with a certain technique on a certain substrate using a certain set of colorants (e.g., inks). If one knows before actually printing what a picture will look like after reproduction, one clearly can save a lot of time and money. For example, a method of predicting the color appearance can be used to display a simulation of the color appearance on a computer display, or to print a simulation of the color appearance on a more easily accessible and cheaper printer as a proof of what is to be printed finally in production.

It is desirable to do this for both reflection printing on an opaque substrate, and transmission imaging on a transparent substrate.

PRIOR ART METHODS

There are various methods found in the prior art that allow one to calculate the color resulting from superimposing a set of colorant layers on a substrate. These methods can be divided in two groups.

First Group of Prior Art Methods

The first group of methods include those that for a particular set of colorants, a particular printing technique (e.g., offset printing on a particular imagesetter), a particular substrate type (e.g., paper, or film for a photographic transparency or print, textile, sheet of plastic, etc.), a particular substrate color (e.g., the color of the paper, or of the transparent film in the case of a transparency, or of the textile, or of the plastic sheet, etc.) and a particular set of colorants and order of printing the colorants, involve printing a relatively large number of overprints of colorants, for example as patches. These patches are measured with a spectrophotometer or calorimeter and the measurements are used to calculate any overprint of colorants in the set using mathematical techniques, for example, interpolation. If carried out well and carefully, these methods can lead to rather accurate results. Modern color management techniques such as Apple Computer's ColorSync™ 2 use such techniques. One drawback is that, depending on how good the mathematical techniques are, one is required to make and measure a large number of color patches, and such a set of patches will only be useful for accurately calculating overprints using the particular colorants and the particular colorant printing order used in the patches. Changing one colorant in the colorant set or changing the order of overprinting typically requires redoing the whole job of printing the set of patches. This printing of the test charts of many patches is expensive and time consuming. Another important drawback is that because of the enormous amount of possible overprint combinations, it is very difficult to characterize sets of more than four colorants, for example printing with seven colors. Such a task demands a large amount of computer memory and work.

Examples of such techniques are described in "Usage of the Chameleon Accelerator for Color Transformations" by J. P. Van de Capelle and L. Plettinck, *Proceedings of the second IS&T/SID Color Imaging conference on Color Science, Systems and Applications,* pp. 165–166, November, 1994.

Another set of prior art techniques are those that use the well known Neugebauer equations for the color of an overprint of colorants. Such methods use measurements of the colorants, all possible overprint combinations of the colorants and the gradation steps of the colorants, so no colorant parameters are determined. These methods also belong to the first group of prior art methods. Neugebauer equations-based methods are known not to produce accurate results.

In summary, while the prior art methods of the first group are capable of calculating overprints of inks, including rastered (i.e., halftoned) inks, the methods do not determine spectral parameters of a colorant that spectrally characterize the colorant.

Second Group of Prior Art Methods

The second group of prior art methods are those that for a fixed substrate and printing technique involve making one or more printouts of each colorant on one or more substrates, measuring the prints, and out of this data extracting a set of one or more parameters for each colorant that can be used to calculate an overprint of each colorant. These methods are applicable only for full (i.e., 100%) coverage of a layer of ink of a particular thickness, and/or are not applicable for variable ink coverages, for example, halftoning at less than 100% dot percentage. In addition, the colorant parameters they determine are not substantially independent of the substrate color for substrates for the same type, e.g., in the case of paper, paper of the same type, weight, texture, and finish, etc.

Perhaps the best known of these uses the two-parameter Kubelka-Munk method. See for example, U.S. Pat. No. 5,428,720, Adams, Jr., inventor (also European Patent application publication EP 0 562 745), entitled "Method and apparatus for reproducing blended colorants on an electronic display," and the publication "Kubelka-Munk Theory and the Prediction of Reflectance," by James H. Nobbs, *Rev. Prog. Coloration*, Vol. 15, pp. 66–75, 1985. The Kubelka-Munk model describes an ink wither by one spectral parameter, $(K/S)(\lambda)$, or by two spectral parameters, scattering $S(\lambda)$ and absorption $\alpha(\lambda)$, where $\lambda$ is the wavelength. In the standard two-parameter theory, for $R_{bg}(\lambda)$ representing the reflectance of the substrate or background, the reflectance $R_1$ resulting from putting the colorant layer with thickness d on top of the substrate is given by:

$$R_t(\lambda) = \frac{1 - R_{bg}(\lambda) * (a(\lambda) - b(\lambda) * \coth(b(\lambda) * S(\lambda) * d))}{a(\lambda) - R_{bg}(\lambda) + b(\lambda) * \coth(b(\lambda) * S(\lambda) * d)}$$

with $$a(\lambda) = \frac{S(\lambda) + \alpha(\lambda)}{S(\lambda)}$$

and $$b(\lambda) = \sqrt{a(\lambda)^2 - 1}.$$

According to the prior art, determining the two colorant parameters involves measuring the spectrum on a bare substrate and on a black substrate, and solving the resulting equations. There also exist in the literature refinements on the two-parameter Kubelka-Munk theory that incorporate internal reflection, anisotropic scattering and other second order effects. However none of these refinements yields spectral parameters $S(\lambda)$ and $\alpha(\lambda)$ that are substantially independent of the substrate color. Thus if the substrate color or type is changed, the characterization process needs to be repeated for printing on the new substrate. In addition, the theory has only be known to be applicable to layers of 100% coverage of colorants of some thickness rather than, for example to halftoned rasters of colorants with less than 100% ink coverage. Thus, the Kubelka-Munk theory has only been applicable to ink layers of different thicknesses, and has not been successful in accurately predicting the color resulting by laying on a substrate different amounts of colorant that may have some microscopic structure, as might occur, for example, in photography (dyes in film emulsions), or in halftone printing (dot rasters), or to inkjet printing (ink particles).

One important advantage of spectrally characterizing colorants by parameters that are substantially invariant for all substrates of the same type, but, for example, not the same color, is that one can treat a substrate with one or more colorant overprints on it as a raw colored substrate of the same type. This simplifies determining the spectral reflection characteristics of overprints of several colorants. For example, given a method for determining the reflection spectrum of a single print of a colorant at some coverage percentage on a raw substrate, one can determine the reflection spectrum of several overprints of several colorants by sequentially applying the model for one colorant. One first determines the reflection spectrum of an overprint of the first colorant on the raw substrate. One now treats the resulting print as a new substrate of the same type but a different color (the color given by the first obtained reflection spectrum) and in the same way determines the reflection spectrum of overprinting a second colorant on top of the first. One can continue this process until one has determined the reflection spectrum of all the overprints of the several colorants. Because the standard one-parameter and two-parameter Kubelka-Munk colorant parameters as determined in the prior art are in practice not substantially substrate-color-independent, such a sequential method for determining overprints would not lead to accurate results if used with these colorant parameters determined according to the prior art. It thus is desirable to find ways of determining colorant parameters that do, in practice, have the substrate color independence property.

Fresnel's formulae for refraction are also noteworthy for comparison. In these formulae, it is considered that for the case of light shining on a substrate on which there are two ink layers, the light is both refracted and absorbed in the ink layers, and that light is reflected both at the boundaries of two ink layers and by the substrate on which the inks are laid. A simplified situation is shown in FIG. 2, where a single ink layer 205 of thickness d is shown laid on a substrate 207 such as paper, which is assumed to be a Lambertian diffuser. The incident beam is shown as 209 traveling first in air 203. Using such a model, one can show that the absorption $\alpha(\lambda)$ can be determined from the following formula:

$$R_t(\lambda) = (1 - \rho_t(\lambda, 45)) * (1 - \alpha)^{(L+d)} * \sum_{i=1}^{\infty} R_p^i(\lambda)(2 * Int)^{(i-1)}$$

where:

$\rho_t(\lambda, 45)$ is the total Fresnel reflection spectrum for both the parallel and orthogonal polarizations of the incident light beam, shown as 209, which is assumed to have an angle of incidence of 45 degrees to the normal 211;

$R_p(\lambda)$ is the reflection spectrum of the substrate measured at 90 degrees;

L is the effective colorant layer thickness for an incident beam at 45 degrees (L=d/cosr;r=45 degrees); and Int incorporates the effect of the light diffusion by the substrate, which is assumed to be Lambertian.

The summation indicates the effect of multiple internal reflections inside the ink layer.

In more mathematical terms, $$\rho_t(\lambda, 45^\circ) = \frac{\left(1-\sqrt{2n^2-1}\right)^2 * \left(n^2+\sqrt{2n^2-1}\right)^2 + \left(1+\sqrt{2n^2-1}\right)^2 * \left(n^2-\sqrt{2n^2-1}\right)^2}{2*\left(1+\sqrt{2n^2-1}\right)^2 * \left(n^2-\sqrt{2n^2-1}\right)^2},$$

where n is the refraction index of the colorant layer, and $$Int = \int_0^{\pi/2} \cos(\varepsilon)*\sin(\varepsilon)\rho_t(\lambda,\varepsilon)*(1-\alpha)^{2*d/\cos(\varepsilon)}d\varepsilon$$

These formulae can be used to calculate the reflection of multiple ink layers on top of one another. Use of a similar but much simpler method to calculate the spectral reflection of one ink on top of a substrate is described in U.S. Pat. No. 5,596,425, Usui, et. al., inventors (also European patent application publication EP 0 669 754), entitled "Method and apparatus for simulating color print." All these techniques are only for a solid ink layer of a particular thickness.

Above mentioned U.S. Pat. No. 5,596,425 also uses a technique based on the extended Phong model that that can be classified in the second group.

All these prior art methods still suffer from relatively low accuracy, and the ones that produce colorant parameters produce colorant parameters that are not substantially independent of the substrate color properties, somewhat reducing the validity and applicability of these parameters.

Yet another technique that can be classified in the second group is the one used in "Predicting the Spectral Behavior of Colour Printers for Transparent Inks on Transparent Support," by P. Emmel, I. Amidror, V. Ostromoukhov, and R. J. Hersch, *Proceedings of the Fourth IS&T/SID Color Imaging Conference on Color Science, Systems and Applications,* pp. 86–91, November 1996. Emmel et al. propose a spectral color method for predicting the color of overprinting transparent inks on a transparent substrate. Their method is based on the determination by measurement of the transmittance spectra of color primaries and the transparent substrate, determining the specific halftoning pattern generated by a particular printer, examining the microscopic structure of the layout of the dots, building a microscopic model of the thickness variations across a single dot, which result in a density function of a single dot of any ink, and applying Beer's absorption law (see, for example, G. Wyszecki and W. S. Stiles, *Color Science: Concepts and Methods, Quantitative Data and Formulae,* Second Edition, New York: John Wiley & Sons, pp. 30–34, 1982). Their model has not been applied to printing on non-transparent substrates or on substrates of different colors or with inks that have scattering characteristics. Prints of the patches of the colorant at different dot percentages and spectral measurements on such prints are not used. One can interpret the result as parameters, which are independent of the dot percentage but dependent on the shape distribution of individual dots. How to deal with reflective surfaces, or with inks that have scattering characteristics, or with printing using a non digital halftoning printing technique is not described.

Thus there still is a need in the art for a method for characterizing the spectral properties of colorants overprinted at a coverage percentage on a reflective or transmittive substrate by a small number of colorant parameters that are a function of the coverage percentage and that are substantially invariant to the substrate color for all substrates of a particular substrate type and for a particular printing technique. Also, there still is a need in the art for a method and apparatus using such characterization for predicting the color of printing a set of colorants at any coverage percentages on a reflective or transmittive substrate.

SUMMARY OF THE INVENTION

Objects of the Invention

An object of this invention is a method for characterizing the spectral properties of colorants when printed on a substrate of a particular type. A further object of this invention is a method for characterizing such spectral properties of colorants by a small number of parameters that are invariant for all substrates of the particular substrate type and that are a function of the coverage percentage. A further object of this invention is a method and apparatus which use such characterization for predicting the color of printing a set of colorants on a substrate. Other objects would be clear from the description below.

Overview of the Invention

These and other objects of the invention are provided for in a method and apparatus for determining a set of colorant parameters that spectrally characterize a colorant in order to predict the color spectrum of an overprint of the colorant laid using a printing technique at a coverage percentage on a substrate of a substrate type, the set of colorant parameters substantially independent of the substrate color. For the example of offset printing using halftoning, these colorant parameters are a function of the dot percentage. At least two parameters are determined for characterizing a non scattering colorant, and at least three are determined for a colorant that has scattering properties. In one aspect of the invention, the method includes making a number of sets of prints of the colorant at a range of coverage percentages on different background colors, for example, different dot percentages for the case of offset printing. The spectra of the prints, for example, the reflection spectra in the case of offset printing, are measured, and equations in the set of parameters are formed and numerically solved for the parameters. In one embodiment, the sets of prints are made on two backgrounds for non scattering colorants and on three backgrounds for scattering colorants. These backgrounds are, in one embodiment, a lightly colored background, a medium colored background, and, for the case of three sets of prints, a dark colored background. In one implementation for offset printing, the three backgrounds are formed by pre-printing the backgrounds, for example, in the case of the medium dark background, using 50% halftone dots with black ink, and in the case of the dark background used for the case of a colorant that has a scattering component, using 100% black ink. For coverage percentages for which prints are not made, interpolation is used to determine the parameters for such colorant coverages.

The equations in the set of the parameters are, in the preferred embodiment, as follows. Denoting a coverage percentage of the range of coverage percentages printed by p, wavelength by $\lambda$, the set of colorant parameters at coverage percentage p by $\alpha_p(\lambda)$ and $\mu_p(\lambda)$ for non-scattering colorants and $\alpha_p(\lambda), \mu_p(\lambda), S_p(\lambda)$ for colorants that have scattering properties, the spectra of the lightly colored substrate, the medium colored substrate, and, when used, the darkly colored substrate by $R_w(\lambda)$, $R_g(\lambda)$, and $R_k(\lambda)$, respectively, and the measured spectra of the p % print of the set of prints on the lightly colored substrate, the medium colored substrate, and when used, the darkly colored substrate by $R_{piw}(\lambda)$, $R_{pig}(\lambda)$, and $R_{pik}(\lambda)$, respectively, the equations are, for the non-scattering case, $$\alpha_p(\lambda) = 1 - \frac{R_{piw}(\lambda)}{R_w^{\mu(p,\lambda)}(\lambda)} \text{ and}$$

$$\mu_p(\lambda) = \frac{\log\left(\frac{R_{piw}(\lambda)}{R_{pig}(\lambda)}\right)}{\log\left(\frac{R_w(\lambda)}{R_g(\lambda)}\right)},$$

and are, for the case of a colorant with a scattering component, $R_{piw}(\lambda)=(1-\alpha_p(\lambda))^*R_w(\lambda)^{\mu p(\lambda)}+S_p(\lambda)$,
$R_{pig}(\lambda)=(1-\alpha_p(\lambda))^*R_g(\lambda)^{\mu p(\lambda)}+S_p(\lambda)$, and
$R_{pik}(\lambda)=(1-\alpha_p(\lambda))^*R_k(\lambda)^{\mu p(\lambda)}+S_p(\lambda)$.

Some colorants, called derived colorants, can be defined by a recipe of concentrations of basic inks. In another aspect of the invention, the set of colorant parameters of a derived colorant is determined by making measurements on a set of dilutions of each of the basic colorants on several backgrounds colors on one or more substrates of the same substrate type, a set of dilutions in this sense possibly including the undiluted basic colorant. The prints that are made of each of the dilutions at different colorant coverages are the same as would be made to determine the colorant parameters of each of the dilutions of the basic colorants. Measurements of the resulting spectra are made. From these, Kubelka-Munk coefficients are determined for the dilutions at the coverage percentages, and, using interpolation, Kubelka-Munk coefficients are determined for the concentrations specified in the recipe of the derived colorant. Then, using the Kubelka-Munk theory for mixtures of colorants, but applied for all the printed coverage percentages, the spectra that would result by printing the derived colorant on the different backgrounds at the different coverage percentages are calculated without actually having to print the derived colorant. From these calculated spectra, using steps analogous to the case of determining the spectral parameters directly, the spectral parameters of the derived colorant are determined.

In another aspect of the invention, a method for using the parameters for determining a single overprint of a colorant on a substrate also is disclosed. Using the result that the colorant parameters are substantially independent of substrate color, in another aspect of the invention, a method is disclosed for determining the spectrum of several overprints of several colorants by sequentially applying the method for one colorant. One first determines the reflection spectrum of an overprint of the first colorant on the raw substrate. One then treats the resulting print as a new substrate of the same type but a different color (the color given by the first obtained reflection spectrum) and in the same way determines the reflection spectrum of overprinting a second colorant on top of the first. One continues this process until one has determined the reflection spectrum of all the overprints of the several colorants.

Yet another aspect of the invention is an apparatus for using the colorant parameters to determine the spectrum of overprints on a substrate of a set of colorants at a set of coverage percentages. The apparatus comprises a first memory for storing the spectrum of the substrate, a logic unit with inputs specifying the coverage percentages and a set of outputs which are the values of the colorant parameters at the coverage percentages. The outputs of the logic unit are coupled to a combiner unit, which also has an input coupled to the first memory. The combiner unit determines the color spectrum of the overprints on the substrate of the set of colorants at the set of coverage percentages. One embodiment of the apparatus described comprises the logic unit being implemented as one or more lookup tables. Another embodiment described comprises the logic unit being implemented as one or more interpolators for determining by interpolation the colorant parameters at the required coverage percentages for each colorant from values of the parameters at a set of fixed values of coverage percentages. The combiner unit is implemented as one or more arithmetic units, each arithmetic unit having an associated background spectrum as an input and a set of colorant parameters at a coverage percentage as another input and determining the spectrum of the overprint of that colorant on a substrate having the associated background spectrum. A parallel implementation is described in which the number of sets of interpolators in the logic unit is the number of colorants and the number of arithmetic units in the combiner unit also is the number of colorants. A serial implementation also is disclosed in which the logic unit comprises a single set of interpolators for a single colorant and the combiner unit comprises a single arithmetic unit for determining a single overprint. The operation of such a serial implementation is that the logic unit and arithmetic unit determine one overprint at a time in sequence, starting with an overprint on the raw substrate, and continuing with the second overprint being on the raw overprint with the first colorant, etc., until all overprints have been determined. After a number of cycles equal to the number of colorant overprints, the output of the arithmetic unit is the spectrum of all the overprints.

Another aspect of the invention is a method and apparatus for simulating the appearance of overprints of a set of colorants on a display using colorant parameters determined according to one or more embodiments of the method of the invention for such determination. One embodiment of the method includes the steps of determining the spectrum of the overprints according to one or more of the above embodiments for determining the spectrum of overprints, and from the spectrum, determining the CIE-XYZ values of the overprint using CIE illuminant-observer weightings, and converting these XYZ values to RGB values to drive a CRT monitor using matrix multiplication and, in some embodiments, also one-dimensional lookup tables. Another aspect of the method includes using a matrix multiplier, one dimensional lookup tables, a multidimensional lookup table and interpolation for converting the XYZ values to the device dependent color values needed to drive a proof printer. One embodiment of the apparatus includes an apparatus for determining the spectrum of the overprints according to one or more of the above embodiments, and multiplier adders for determining the CIE-XYZ values of the overprint using CIE illuminant-observer weightings, and a matrix multiplier and, in some embodiments, also one dimensional lookup tables to produce RGB values to drive a CRT monitor. Another aspect of the apparatus includes a matrix multiplier, one dimensional lookup tables, a multidimensional lookup table and a multidimensional interpolator for converting the XYZ values to the device dependent color values needed to drive a proof printer.

These and other objects, features, aspects and advantages of the present invention will become more apparent from the following detailed description of preferred embodiments with the accompanying drawings.

DETAILED DESCRIPTION OF THE PREFERRED EMBODIMENTS

A preferred embodiment of the present invention is a method implemented on a computer. The steps of the method are performed by the computer executing a software program.

Figure 1:
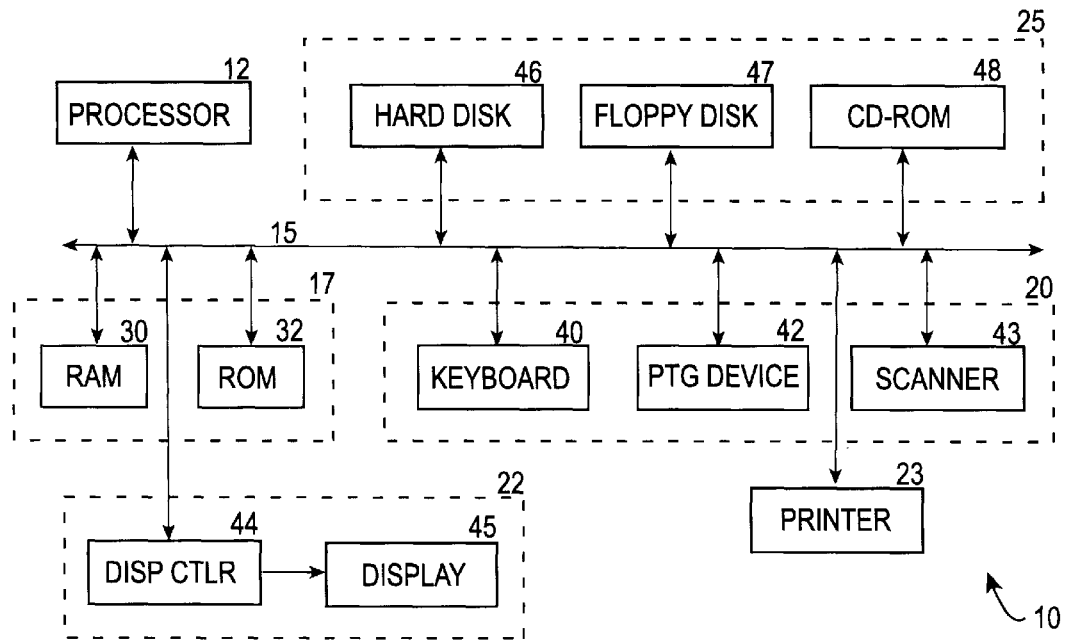
FIG. 1 is a block diagram of a typical computer system in which the present invention may be embodied.
Figure 2:
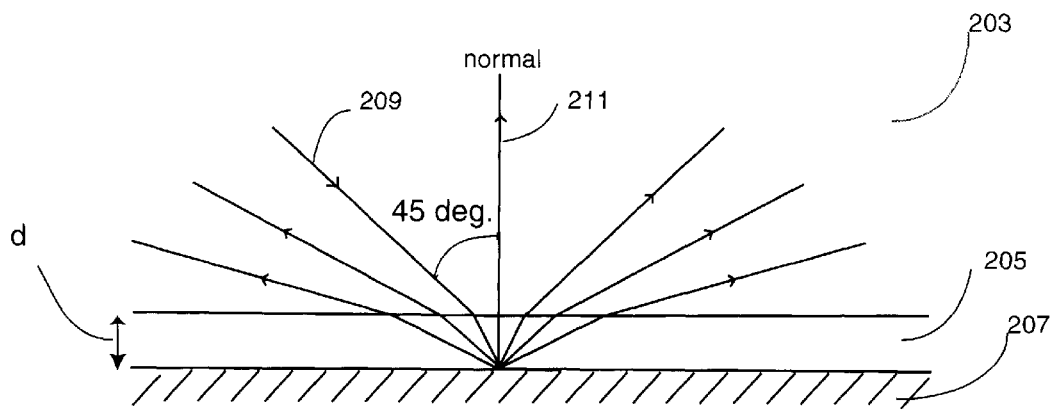
FIG. 2 shows the reflection through an ink layer on a substrate that acts as a Lambertian diffuser.

FIG. 1 is a simplified block diagram of a computer system 10 in which the present invention may be embodied. The computer system configuration illustrated at this high level is standard, and as such, FIG. 1 is labeled "PRIOR ART." A computer system such as system 10, suitably programmed to embody the present invention, however, is not prior art. The specific embodiments of the invention are embodied in a general-purpose computer system such as shown in FIG. 1, and the remaining description will generally assume that environment. However, the invention may be embodied in dedicated devices such as printer servers, and printer controllers.

In accordance with known practice, the computer system includes a processor 12 that communicates with a number of peripheral devices via a bus subsystem 15. These peripheral devices typically include a memory subsystem 17, a user input facility 20, a display subsystem 22, output devices such as a printer 23, and a file storage system 25.

In this context, the term "bus subsystem" is used generically so as to include any mechanism for letting the various components of the system communicate with each other as intended. With the exception of the input devices and the display, the other components need not be at the same physical location. Thus, for example, portions of the file storage system could be connected via various local-area or wide-area network media, including telephone lines. Similarly, the input devices and display need not be at the same location as the processor, although it is anticipated that the present invention will most often be implemented in the context of personal computers (PCs) and workstations.

Bus subsystem 15 is shown schematically as a single bus, but a typical system has a number of buses such as a local bus and one or more expansion buses (e.g., ADB, SCSI, ISA, EISA, MCA, NuBus, or PCI), as well as serial and parallel ports. Network connections are usually established through a device such as a network adapter on one of S these expansion buses or a modem on a serial port. The computer system may be a desktop system or a portable system or an embedded controller.

Memory subsystem 17 includes a number of memories including a main random access memory ("RAM") 30 and a read only memory ("ROM") 32 in which fixed instructions are stored. In the case of Macintosh-compatible personal computers this would include portions of the operating system; in the case of IBM-compatible personal computers, this would include the BIOS (basic input/output system).

User input facility 20 typically includes a keyboard 40 and may further include a pointing device 42 and a scanner 43. The pointing device may be an indirect pointing device such as a mouse, trackball, touchpad, or graphics tablet, or a direct pointing device such as a touchscreen incorporated into the display.

Display subsystem 22 typically includes a display controller 44 and a display device 45 coupled to the controller. The display device may be a cathode ray tube ("CRT"), a flat-panel device such as a liquid crystal display ("LCD"), or a projection device. Display controller 44 provides control signals to display device 45 and normally includes a display memory (not shown in the figure) for storing the pixels that appear on the display device.

The file storage system provides persistent (non-volatile) storage for program and data files, and typically includes at least one hard disk drive 46. There may also be other devices such as a floppy disk drive 47, a CD-ROM drive 48 and optical drives. Additionally, the system may include hard drives of the type with removable media cartridges. As noted above, one or more of the drives may be located at a remote location, such as in a server on a local area network or at a site on the Internet's World Wide Web.

The Single Colorant Case

The first case considered is characterizing by a small number of spectral parameters the spectral properties of a colorant for printing the colorant with a particular printing technique on a substrate. Some colorants so printed can be considered non-scattering. Such colorants can be characterized according to one aspect of this invention by two spectral parameters. Colorants that have scattering properties can be characterized according to another aspect of this invention by three spectral parameters. More than two spectral parameters might be necessary for some non-scattering colorants, and more than three spectral parameters might be necessary for some scattering colorants. This invention is not limited to characterizing colorants by any particular maximum number of parameters.

While the description of the preferred embodiment is for a reflective image as would occur with printing with a colorant such as a dye or pigment based ink, on a substrate type such as paper of a particular type, plastic of a particular type, fabric of a particular type, or ceramic material of a particular type, using printing techniques such as offset, gravure, flexo, ink jet or dye sublimation, the present invention is not restricted to reflective surfaces. The method and apparatus of the present technique is applicable also to determining the transmittance of colorants when such colorants are laid on or imbedded in a transmitting or semi-transparent substrate, such as transparent or semi-transparent film, as would occur in making photographic transparencies and in printing on a transparent or semi-transparent carrier of a particular type. In such a case, rather than reflection spectra being determined and used, transmittance spectra are used. How to extend the method of the present invention to deal with transmission images would be clear to one of ordinary skill in the art.

One first considers the case of having one non-scattering colorant. The method described for this case is for characterizing the colorant by determining two colorant parameters for a particular printing technique on a particular substrate type. It should be noted that while the resulting parameters are invariant to the substrate color, they normally would only be expected to be valid for the particular printing technique for printing on a particular substrate type. For example, the colorant parameters determined for offset printing on a paper of a particular composition, weight, texture, and finish, would apply to all such papers independent of the paper color, but not necessarily to other paper types or for another printing technique.

In the first embodiment of the method of the present invention, one determines parameters of the colorant by printing two sets of patches at different coverage percentages, one on a substrate of a first substrate color as determined by the substrate's reflection spectrum (for reflection printing) or transmission spectrum (for printing transparencies), and the second set of patches on a substrate of the same type but of a second substrate color different from the first substrate color. In one embodiment, the substrate of the first substrate color is a lightly colored (e.g., white) substrate and, and the substrate of the second color is a medium colored substrate, the lightly colored and medium colored substrates being of the same substrate type. In the preferred embodiment, the medium colored substrate is a greyish substrate. Each set of patches goes from 0% to 100% colorant (e.g., ink) coverage (e.g., dot percentages for ink) in steps of 10% increments. Other embodiments may include fewer or more patches, with equal or unequal increments of ink coverage. Also, in the preferred embodiment, the printing of the patches is using halftone printing as would occur with offset printing, so that a patch of p % ink coverage means a halftone screen of a dot percentage of p %. The method is not limited to halftone printing. One can apply the method to modulated printing, such as color laser printing and dye sublimation printing. In such cases, for example, instead of a p % dot percentage screen, one would print an area of p % modulated colorant intensity. The method also applies to photographic printing and transparency making, in which case colorant coverage would represent the amount of photographic colorant. How to extend the methods of the present invention to non-screened printing would be clear to those of ordinary skill in the art.

Figure 3:
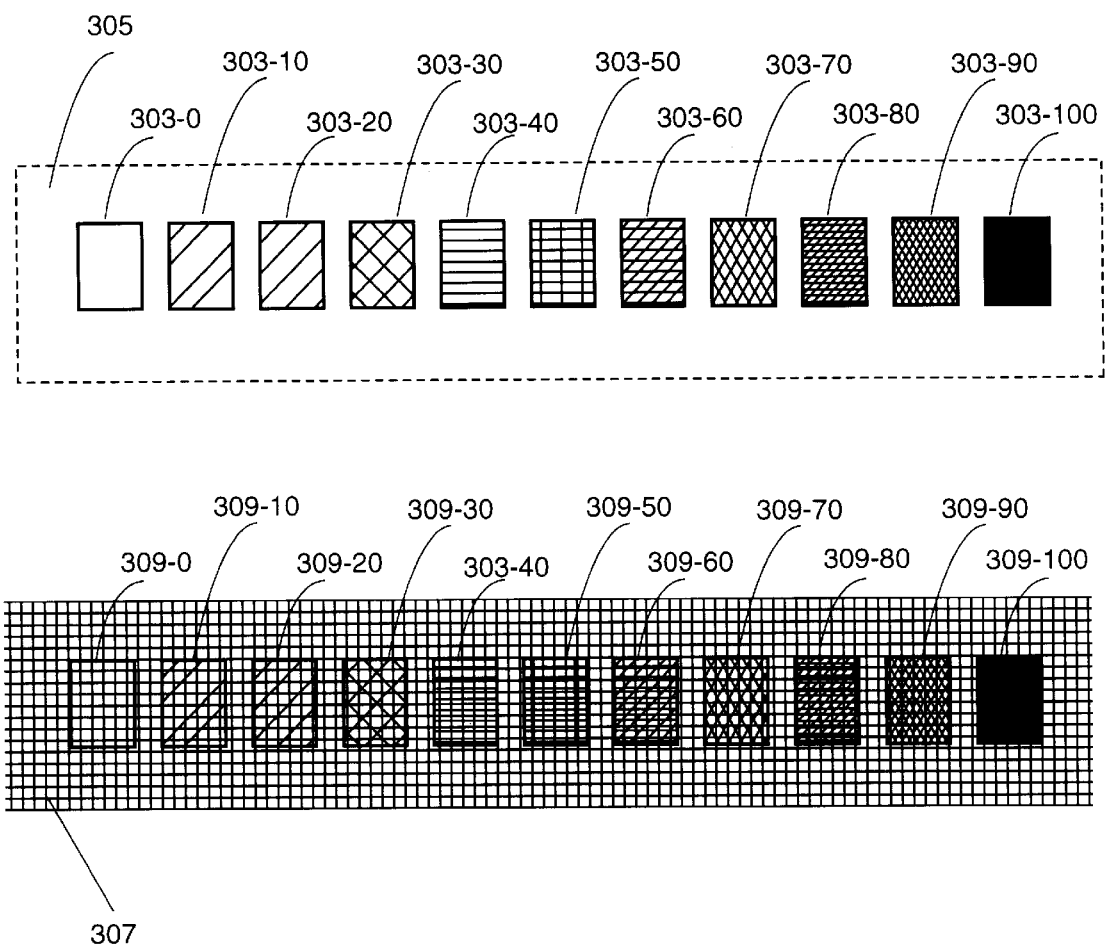
FIG. 3 shows the prints made in order to determine the colorant spectral parameters $\alpha(p, \lambda)$ and $\mu(p, \lambda)$ according to one embodiment of the method of the present invention.

While the method calls for printing on two substrates of different color of the same substrate type, in particular on a lightly colored and a medium colored substrate of a particular substrate type, in the preferred embodiment, the medium colored substrate is obtained by printing on the lightly colored substrate with a colored colorant. In particular, the medium colored substrate is a greyish substrate and is obtained by printing on the lightly colored substrate with a strip of 50% black with the back colorant (e.g., black ink) to give a medium colored strip. Alternatively, a grey colorant may be laid over the lightly colored substrate to provide a medium colored substrate. For notational simplicity, the lightly colored substrate will be called "virgin," "blank," or "white" herein, and the medium colored substrate will be called "grey." In the case of the preferred embodiment of halftone printing, by 50% is meant a screen of 50% ink coverage of black, as would commonly be understood by those of ordinary skill in the art. Again, when applying the method to modulated printing, such as color laser printing, or photography or dye sublimation printing, instead of a 50% dot percentage screen, one would print an area of 50% modulated colorant density. One prints two rasters (sets) of patches, one on white (virgin, blank) substrate and one on top of the grey strip. Each set of patches goes from 0% to 100% ink coverage (e.g., dot percentage) in steps of 10% increments. This is shown in FIG. 3. There are now twenty two patches, eleven patches, denoted 303-0 through 303-100, indicating 0% through 100% coverage, respectively, on white substrate 305, and eleven patches, denoted 309-0 through 309-100, indicating 0% through 100% coverage, respectively, on top of the grey area 307.

The spectral characteristics of each of the twenty-two colors of the twenty-two patches are now measured using any instrument capable of measuring the reflection spectrum. In the preferred embodiment, a spectrophotometer is used, although other instruments such as a spectroradiometer may be used. Also, as would be clear to those of ordinary skill in the art, in the case of transmission imaging, transmission spectra are measured, and any instrument capable of measuring transmission spectra may be used. Each patch print of a particular coverage percentage is considered to be a colorant layer. That is, one ignores the microscopic look (the halftone pattern, etc.) of each patch. This is not done, for example, with the Kubelka-Munk theory of the prior art, which applies only to actual colorant layers. Thus one has eleven colorant layers denoted p %, with p=0, 10, 20, ..., 100, and for each coverage percentage there are two measurements, and in addition two measurements common to all layers. These measurements are denoted as follows:

$R_{pig}(\lambda)$: the reflection spectrum as a function of wavelength $\lambda$ for the p % layer on grey, with p=0, 10, 20, ..., 100;

$R_{piw}(\lambda)$: the reflection spectrum as a function of wavelength $\lambda$ for the p % layer on white, with p=0, 10, 20, ..., 100;

$R_g(\lambda)$: the reflection spectrum as a function of wavelength $\lambda$, of grey; and $R_w(\lambda)$: the reflection spectrum as a function of wavelength $\lambda$, of white.

For each of these colorant layers, one now calculates two spectral parameters $\alpha$ and $\mu$ for the colorant as follows:

$$\alpha_p(\lambda) = 1 - \frac{R_{piw}(\lambda)}{R_w^{\mu(p,\lambda)}(\lambda)}, \; p = 0, 10, \ldots, 100 \quad \text{Eqn. (1a)}$$

with $$\mu_p(\lambda) = \frac{\log\left(\frac{R_{piw}(\lambda)}{R_{pig}(\lambda)}\right)}{\log\left(\frac{R_w(\lambda)}{R_g(\lambda)}\right)}. \quad \text{Eqn. (1b)}$$

Note that the coverage percentage p appears as a subscript in these equations to indicate that the above quantities and equations are for a patch with coverage percentage p. When p appears as an argument of the function, it means any value of p, including colorant coverage percentages which were not printed and for which no measurements were made. In one embodiment, for such colorant coverage percentages which were not measured, one determines the reflection spectra for the prints on white and on grey by interpolating between the reflection spectra of the colorant coverage percentages that were measured. Out of these calculated reflection spectra one can then calculate the colorant parameters using $$\alpha(p, \lambda) = 1 - \frac{R_{iw}(p, \lambda)}{R_w^{\mu(p,\lambda)}(\lambda)}, \quad \text{Eqn. (1c)}$$

with $$\mu(p, \lambda) = \frac{\log\left(\frac{R_{iw}(p, \lambda)}{R_{ig}(p, \lambda)}\right)}{\log\left(\frac{R_w(\lambda)}{R_g(\lambda)}\right)} \quad \text{Eqn. (1d)}$$

which are the same as Eqns. (1a) and (1b) except that in these, the coverage percentage appears as an argument of a function rather than a subscript, indicating that these equations are not only for values of p that were printed.

In another embodiment, one determines the spectral parameters of the colorant for any non-measured required coverage percentage by interpolating between the spectral parameters of the colorant for the coverage percentages which were measured.

Thus one ends up with two spectral functions $\alpha(p, \lambda)$ and $\mu(p, \lambda)$, forming a set of parameters for the particular colorant, where p is the coverage percentage of the colorant (dot percentage in the case of halftone printing). The set of parameters takes into account some of the interaction of the colorant with the substrate, with the discovered result that the two parameters are substantially invariant with respect to the substrate color (i.e., substrate spectral characteristics). That is, repeating the above experiment by printing on several different substrates of the same general substrate type, but of different spectral characteristics (e.g., different color), within a range of interest, it was observed that for most colorants of interest, the two spectral parameters for any colorant remained essentially the same for all of the different substrate colors.

Thus, a method has been disclosed for characterizing a colorant by two parameters when the colorant is laid on a substrate of a particular substrate type, the characterization and the parameters dependent only on the substrate type and substantially independent of the substrate color.

One can then calculate the reflectance spectrum $R_p(\lambda)$ of p % of the overprint of a particular colorant on a substrate type, with $R_{bg}(\lambda)$ representing the reflectance of the substrate, as follows:

$$R_p(\lambda) = (1-\alpha(p, \lambda)) * R_{bg}(\lambda)^{\mu(p,\lambda)}. \quad \text{Eqn. (2)}$$

One then can apply Eqn. (2) to determine an overprint formed by laying down different colorants in a particular order on the substrate. One starts with $R_{bg}(\lambda)$ representing the reflectance of the raw substrate, and uses Eqn. (2) to determine as $R_p(\lambda)$, $R_{p1}(\lambda)$ of p1% of the first colorant applied. One now repeats the calculation by substituting for $R_{bg}(\lambda)$ in Eqn. (2) the $R_{p1}(\lambda)$ obtained by laying down the first colorant on the substrate, and calculating a new $R_p(\lambda)$, $R_{p2}(\lambda)$ representing the result of laying down p2% of a second colorant. This can be repeated for a number of colorants in different amounts laid on a substrate in different order.

The above description is for non-scattering colorants that can be characterized by two parameters ($\alpha$, $\mu$). For some colorants, in particular, those that exhibit scattering properties, a third parameter, S for scattering, also needs to be used. For printing on a reflective substrate, colorants that exhibit scattering characteristics will result, when they are printed on black, in a reflection spectrum that in some regions shows higher reflection than the reflection spectrum of black itself. Also, colorants that do not have scattering characteristics have a value 0 for the third parameter S.

For colorants that have scattering characteristics, in an alternate embodiment, one prints gradation steps of the colorant on three different backgrounds: a substrate of a first color of a particular substrate type, a substrate of a second color of a particular substrate type, and a substrate of a third color of a particular substrate type, where the first, second and third colors are different. In one embodiment, the substrates of the first, second and third colors are a lightly colored, a medium colored, and darkly colored substrate, respectively, all of the same substrate type. In one embodiment, the lightly colored, medium colored, and darkly colored substrates are, respectively, white, greyish and blackish substrates.

Figure 4:
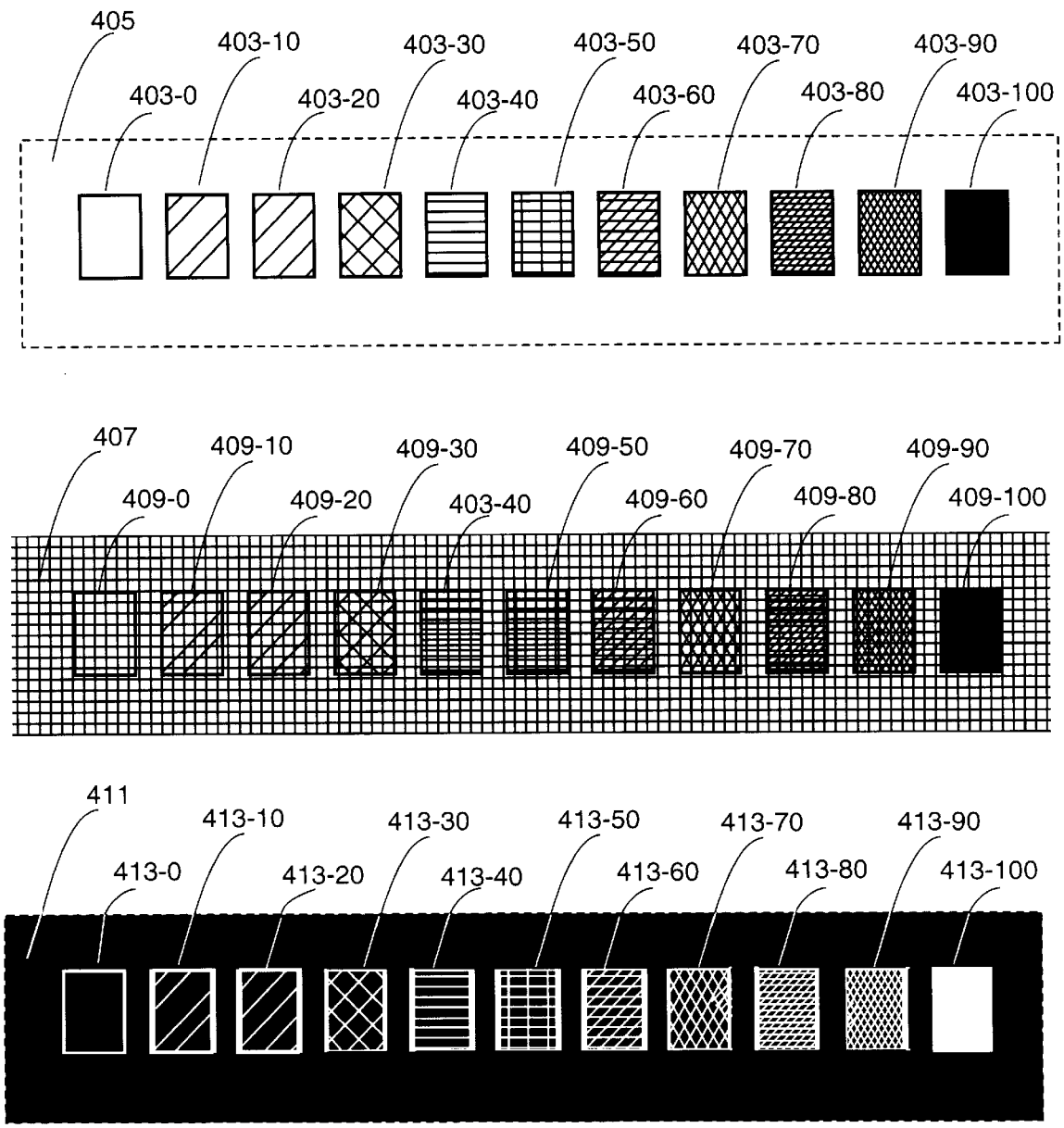
FIG. 4 shows the prints made in order to determine the colorant parameters $\alpha(p, \lambda)$, $\mu(p, \lambda)$ and $S(p, \lambda)$ according to one embodiment of the method of the invention.

The printing of the gradation steps on the three backgrounds is shown in FIG. 4. Shown on white substrate 405 are eleven patches, denoted 403-0 through 403-100, with 0% through 100% coverage, respectively. Also shown on greyish substrate 407 are eleven patches, denoted 409-0 through 409-100, with 0% through 100% coverage, respectively. Finally, also shown on blackish substrate 411 are eleven patches, denoted 413-0 through 413-100, with 0% through 100% coverage, respectively. The grey and black can be obtained by printing on a white substrate with grey and black colorants, or as in the preferred embodiment and for the case of offset printing using halftone, by printing a medium halftone screen and a dark halftone screen using black colorant.

In one embodiment, from the gradation steps, one determines three colorant parameters $\alpha_p(\lambda)$, $\mu_p(\lambda)$ and $S_p(\lambda)$ through a numerical fitting technique. In this, one models $R_{pik}$, $R_{pig}$, and $R_{piw}$, and in the particular embodiment, the models used are as follows:

$$R_{piw}(\lambda) = (1-\alpha_p(\lambda)) * R_w(\lambda)^{\mu p(\lambda)} + S_p(\lambda), \quad \text{Eqn. (3a)}$$

$$R_{pig}(\lambda) = (1-\alpha_p(\lambda)) * R_g(\lambda)^{\mu p(\lambda)} + S_p(\lambda), \text{ and} \quad \text{Eqn. (3b)}$$

$$R_{pik}(\lambda) = (1-\alpha_p(\lambda)) * R_k(\lambda)^{\mu p(\lambda)} + S_p(\lambda). \quad \text{Eqn. (3c)}$$

One measures the spectral characteristics of each of the thirty-three colored patches. Each patch print of a particular percentage coverage is considered to produce a colorant layer, and one ignores the microscopic look (the halftone pattern, etc.) of each patch. Thus one has eleven colorant layers denoted p %, with p=0, 10, 20, . . . , 100, and for each coverage percentage, there are three measurements, and in addition three measurements common to all layers. These measurements are denote as follows::

$R_{piw}(\lambda)$: the reflectance spectrum of p % patch on white;
$R_{pig}(\lambda)$: the reflectance spectrum of p % patch on grey;
$R_{pik}(\lambda)$: the reflectance spectrum of p % patch on black;
$R_w(\lambda)$: the reflectance spectrum of white;
$R_g(\lambda)$: the reflectance spectrum of grey; and
$R_k(\lambda)$: the reflectance spectrum of black.

One measures $R_{pik}$, $R_{pig}$, $R_{piw}$, $P_w$, $R_g$ and $R_k$ with, for example, a spectrophotometer, and using these measurement, one determines the best fit of parameters $\alpha p(\lambda)$, $\mu p(\lambda)$ and $S_p(\lambda)$, that minimize the cost function that reflects the difference between calculated and measured values of $R_{pik}$, $R_{pig}$, $R_{piw}$. The resulting equations are solved for $\alpha p(\lambda)$, $\mu p(\lambda)$ and $S_p(\lambda)$ in the preferred embodiment using the well known numerical technique of conjugate directions with the measurements of $R_{pik}$, $R_{pig}$, $R_{piw}$, $P_w$, $R_g$ and $R_k$ as known parameters. Other numerical methods, such as the method of steepest descent, etc., may also be used. In the preferred embodiment, the spectra are sampled in $\lambda$, and in particular, $n_l=36$ wavelengths are used for these spectra: 380 nm, 390 nm, 400 nm, . . . , 720 nm, and 730 nm. The particular error function Err used for the conjugate directions minimization is $$\text{Err}(\lambda)=(R'_{piw}(\lambda)-R_{piw}(\lambda))^2+(R'_{pig}(\lambda)-R_{pig}(\lambda))^2+(R'_{pik}(\lambda)-R_{pik}(\lambda))^2$$

where the quantities $R_{piw}'(\lambda)$, $R_{pig}'(\lambda)$, and $R_{pik}'(\lambda)$ indicate the spectra calculated according to Eqns. (3a–3c) above, and the non-primed quantities $R_{piw}(\lambda)$, $R_{pig}(\lambda)$, and $R_{pik}(\lambda)$ are the measured reflection spectra. For a description of the conjugate directions techniques, see for example, *Numerical Recipes in C: The Art Of Scientific Computing*, by William H. Press, Brian P. Flannery, Saul A. Teukolsky and William T. Vetterling, 2nd. Edition, Cambridge University Press, pp. 310 ff, 1990. Many other best fit numerical techniques can also be used. Also, other error functions are possible within the scope of this aspect of the invention. In another embodiment, an error function that gives a higher weighting to the error of the prints on white than the weightings on the grey and black colored substrates is used. In yet another embodiment, there may be many background colors used, indicated, for example, by letters a, b, . . . , and in such a cases, the error function may contain more terms to account for these backgrounds, for example, $$\text{Err}(\lambda)=(R'_{piw}(\lambda)-R_{piw}(\lambda))^2+(R'_{pig}(\lambda)-R_{pig}(\lambda))^2+(R'_{pik}(\lambda)-R_{pik}(\lambda))^2+(R'_{pia}(\lambda)-R_{pia}(\lambda))^2+(R'_{pib}(\lambda)-R_{pib}(\lambda))^2+ \ldots$$

In a second embodiment for the three parameter case, one again measures the spectral characteristics of each of the thirty-three colored patches. Again, each patch print of a particular percentage coverage is considered to produce a colorant layer, and one ignores the microscopic look (the halftone pattern, etc.) of each patch. Thus one has eleven colorant layers denoted p %, with p=0, 10, 20, . . . , 100, and for each coverage percentage there are three measurements, and in addition three measurements common to all layers. These measurements are denoted, as before, $R_{piw}(\lambda)$, $R_{pig}(\lambda)$, $R_{pik}(\lambda)$, $R_w(\lambda)$, $R_g(\lambda)$, and $R_k(\lambda)$.

One now calculates three spectral parameters for each of the basic colorants as follows:

$$S_p(\lambda) = R_{pik}(\lambda) - R_k(\lambda), \qquad \text{Eqn. (4a)}$$

$$\alpha_p(\lambda) = 1 - \frac{R'_{piw}(\lambda)}{R_w^{\mu_p(\lambda)}(\lambda)}, \qquad \text{Eqn. (4b)}$$

and $$\mu_p(\lambda) = \frac{\log\left(\frac{R'_{piw}(\lambda)}{R'_{pig}(\lambda)}\right)}{\log\left(\frac{R_w(\lambda)}{R_g(\lambda)}\right)}, \qquad \text{Eqn. (4c)}$$

with $$R'_{piw}(\lambda) = R_{piw}(\lambda) - S_p(\lambda), \text{ and} \qquad \text{Eqn. (4d)}$$

$$R'_{pig}(\lambda) = R_{pig}(\lambda) - S_p(\lambda). \qquad \text{Eqn. (4e)}$$

For coverage percentages (e.g., dot percentages) which were not measured, as in the case of a single colorant above, in one embodiment, one determines the reflection spectra for the prints on white, on grey and on black by interpolating between the reflection spectra of the dot percentages that were measured. Out of these calculated reflection spectra one can then calculate the colorant parameters as described above in Eqns. (4a–4e). In another embodiment, one determines the spectral parameters of the colorant for any non-measured required coverage percentage by interpolating between the spectral parameters of the colorant for the coverage percentages which were measured.

The set of colorant parameters determined as described takes into account some of the interaction of the colorant with the substrate, with the important result that the colorant parameters of the colorant are essentially independent of the substrate color for all substrates of a particular type. As a consequence, one can calculate the color reflection spectrum $R_p(\lambda)$ resulting from printing the colorant with parameters $\alpha(p, \lambda)$, $\mu(p, \lambda)$, and $S(p, \lambda)$, with amount of ink (e.g., dot percentage)p on the substrate being considered, for the particular printing technique and for a particular substrate of a particular type having substrate color reflection spectrum $R_{bg}(\lambda,)$, using a formula such as:

$$R_p(\lambda)=(1-\alpha(p, \lambda))*R_{bg}(\lambda)^{\mu(p,\lambda)}+S(p, \lambda). \qquad \text{Eqn. (5)}$$

To predict the color resulting from printing multiple inks consecutively with a certain ink coverage (e.g., dot percentage) on top of each other, the invariance property of the colorant parameters is used. One can regard a substrate with a colorant printed on it as a substrate of the same type, but having a different color, and one can now determine the color spectrum of laying a second colorant over this first colorant. Thus, according to one embodiment of the method of this invention, to predict the color resulting from printing multiple inks consecutively with a certain ink coverage (e.g., dot percentage) on top of each other, the method applies Eqn. (5) repeatedly in the particular printing order. That is, one then applies Eqn. (5) to determine an overprint formed by laying down different colorants in a particular order. One starts with $R_{bg}(\lambda)$ representing the reflectance of the raw substrate, and uses Eqn. (5) to determine as $R_p(\lambda)$, $R_{p1}(\lambda)$ of $p_1$% of the first colorant applied. One now repeats the calculation by substituting for $R_{bg}(\lambda)$ in Eqn. (5) the $R_{p1}(\lambda)$ obtained by laying down the first colorant on the substrate, and calculating a new $R_p(\lambda)$, $R_{p2}(\lambda)$ representing the result of laying down $p_2$% of a second colorant. This can be repeated for a number of colorants in different amounts laid on a substrate in different order.

As stated earlier, for some colorants, more than three parameters may be necessary to characterize printing of the colorant on a substrate of a substrate type with the parameters substantially independent of the substrate color. How to extend the above embodiments of the method of the invention for such cases would be clear to those of ordinary skill in the art. For example, for a colorant for which four spectral parameters are needed, four or more sets of prints would be made of four substrates of different background colors. Measurement of the resulting reflection spectra would lead to four equations in the four unknowns for any wavelength and printed coverage percentage, which can be solved by a variety of numerical methods.

Also clear to those of ordinary skill in the art would be that if the colorant parameters need to be determined for only a range of coverage percentages rather than for any coverage percentage, than, in another aspect of the method of the invention, the sets of prints of the colorants only would need to cover the particular range of interest of coverage percentages.

A key feature in the embodiments described herein is making sets of prints of a colorant at different coverage percentages on background colors on a substrate, measuring the color of the prints, in particular, the color spectrum, and, using a relationship relating the spectrum of the print at a coverage percentage of the colorant to the spectrum of the background color and the colorant parameters at that coverage percentage, setting up a set of equations to solve for the colorant parameters at that coverage percentage. The relationship uses the key property of the colorant parameters that they are substantially independent of the color of the substrate for a particular substrate type. In the preferred embodiments described herein, for the two-parameter case, the relationship takes the form of Eqn. (2), while for the three parameter case, the relationship takes the form of Eqn. (5). Other embodiments are possible within the scope of the invention that use a different relationship for the relationship relating the spectrum of the print at a coverage percentage of the colorant to the spectrum of the background color and the colorant parameters at that coverage percentage, thus providing an alternate set of parameters.

Also included in the scope of the embodiments of the present invention for determining colorant coefficients are those variations of the method where, for the case of determining $n_p$ colorant parameters for any colorant, more than $n_p$ sets of prints are made, leading to more than $n_p$ equations which can be solved for the parameters. Implementing such embodiments would be clear to those of ordinary skill in the art from the description herein.

The Derived Colorant Case

The above-described embodiment of the method of the present invention for the single colorant case allows one to characterize individual colorants by parameters that are substantially independent of the color of the substrate on which they are laid, and to use these parameters, to predict the color when laying a so-characterized colorants on a substrate of the same particular type as the substrate used in the characterization. This essential invariance of the colorant parameter with respect to the substrate color for a given substrate type also leads to a method to predict the color when laying several so characterized colorants on a substrate of a particular type since any overprint can be considered as a colored substrate of the same type. The characterization thus leads to a method for predicting the spectral characteristics of overprints of such characterized colorants.

Figure 5:
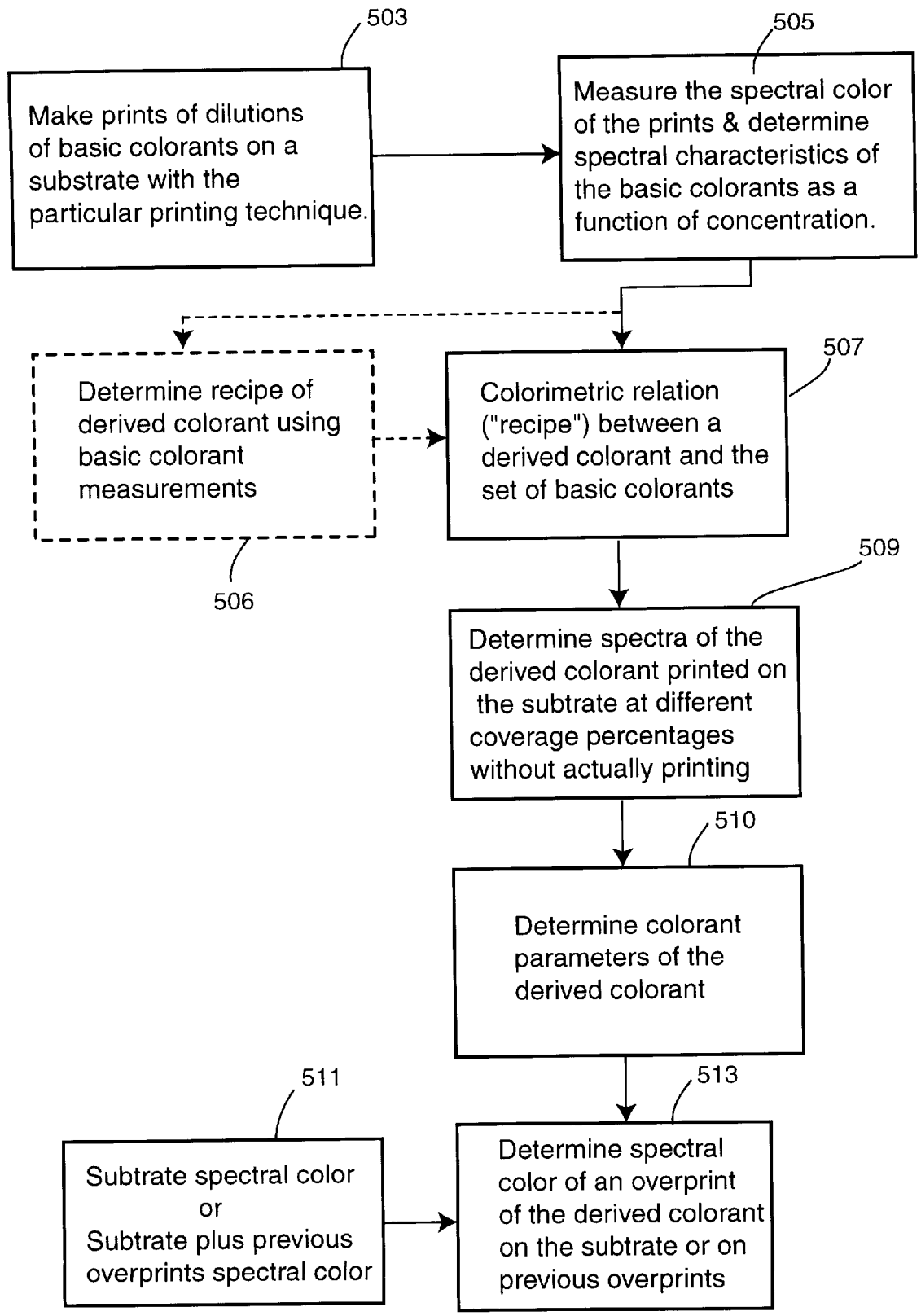
FIG. 5 shows a flowchart of the general steps of calculating the spectral color resulting from superimposing a colorant layer on a colored carrier, according to one embodiment of the method of the invention.

Another aspect of the present invention is now described. In particular, a modification of the method is described which allows one to characterize a much larger set of colorants, and then determine overprints of such colorants. In particular, one can characterize any of a large set of colorants, called "derived colorants," whose color characteristics can be matched by mixing a small set of colorants, called "basic colorants," according to a recipe. The overall method is illustrated in FIG. 5. In step 503, a set of patches is made with varying amounts of each of the set of basic colorants on the particular substrate type of interest for a set of dilutions of the colorant. In step 505, measurements are made on the set of patches, and, treating each dilution and each coverage percentage as if it was a different colorant, spectral characterizations of each printed coverage percentage of each of the basic colorants is determined as a function of dilution. Using these characterizations of the basic colorants and knowledge of the recipe, shown as box 507, of how any derived colorant which is not a basic colorant is matched or made with basic colorants, one then determines in step 509 the spectra of a set of patches of varying raster percentages of the derived colorant on the particular substrate type of interest as if the set of patches printed in step 503 was printed with the derived colorant, and using these spectra, one also determines in step 510 the colorant parameters of the derived colorant. In step 513 one uses these colorant parameters to determine the reflection (or transmission) spectra for certain amounts of the derived colorant for a particular printing technique on a particular substrate type of a known color spectrum, shown as 511, without needing to make measurements or prints (or transparencies) using the derived colorant. If the recipe for the derived colorant is not known, then the method includes step 506 (shown dotted) of using knowledge of the desired color and determining the recipe from such knowledge and some of the measurements of the basic colorants of step 505. Thus, using steps 503, 505, 506 (when needed), 507, 509 and 510, one can characterize a very large number of possible colorants by making measurements on only a smaller set of basic colorants. In another aspect of the method, one can repeat steps 511 and 513 to determine the reflection (or transmission) spectra for certain coverage percentages of an additional derived colorant laid over the first derived colorant. In this case, known spectrum 511 is the spectrum of the substrate and the first derived colorant, as determined in the first application of step 513. As before, the description of the preferred embodiment is for a reflective image as would occur with printing on a substrate like paper, the present invention is not restricted to reflective surfaces. The method and apparatus of the present technique is applicable also to determining transmittance of colorants when such colorants are laid on a transmitting or partially transmitting substrate, such as film. In such a case, rather than reflection spectra being determined and used, transmittance spectra are used. How to extend the method of the present invention to deal with transmission images would be clear to one of ordinary skill in the art.

The preferred embodiment of the method of this invention applied to derived colorants is now described in more detail. The method starts by selecting a set of basic colorants. These basic colorants are selected so that they span the gamut of all the colorants (i.e., the derived colorants) for which characterizations are desired for the particular printing technique on the particular substrate type. In the preferred embodiment, for printing on a particular paper, a set of basic colorants were chosen from a larger set of colorants by elimination. The process is described as follows: One removes a colorant out of the large set if that colorant can be made by mixing two or more colorants out of the remainder of the set. This process is continued until no colorant in the set can be made by mixing two or more colorants out of the set. The set of colorants thus obtained is a set of basic colorants.

In one embodiment applicable to the case of printing proofs on glossy proof paper, in particular, that sold under the trademark "CROMALIN," the set of ink powders made by basic "CROMALIN" were used as the basic colorants. For the case of offset printing using some type of inks, for example "TOYO" brand inks for paper, the set of basic ink supplied by the manufacturer, for example "TOYO," for such offset printing would be used. Similarly, for printing on textiles using some colorant made for printing on a particular material, e.g., polyester cloth, the basic inks for that particular type of printing would be used.

As mentioned in the above description for the single colorant case, some colorants can be characterized by two parameters ($\alpha$, $\mu$), while others, in particular, those that exhibit scattering properties, are characterized by three parameters, ($\alpha$, $\mu$, S). The particular embodiment described herein for determining derived colorants is for the case that the basic colorants are characterized by three parameters. How to carry out this aspect of the method of the present invention for basic colorants that may be characterized by two-parameters or by more than three parameters would be clear to those of ordinary skill in the art.

One now uses measurements of prints of these basic colorants to determine the characterization of any colorant of a larger set of colorants, characterized by each being in the gamut spanned by the selected basic colorants, that is, for any derived colorant. One simple case is when a derived colorant has a one-to-one relationship with one of the selected basic colorants, that is, can be expressed as some function of only that selected basic colorant. In such a case, the colorant parameters for the derived colorant are the colorant parameters of the basic colorant, and one thus may determine the colorant parameters of that basic colorant in the same way as described above. That is, in the preferred embodiment, one makes (e.g., prints) gradation steps of the basic colorant on three different backgrounds, a lightly colored, medium colored, and darkly colored substrate of the same type, lightly colored, medium colored, and darkly colored called white, grey and black, respectively. See FIG. 4. The grey and black can be grey and black substrates or obtained by printing on a white substrate with grey and black colorants, or by printing a medium halftone screen and a dark halftone screen using black colorant, for the case of offset printing using halftone. In the preferred embodiment, the latter approach is used. That is, one first makes (one prints in the preferred embodiment) strips of 100% black, 50% black (i.e., grey) and 0% black (i.e., white), shown as areas 411, 407, and 405, respectively. For the basic colorant, one prints three rasters (i.e., sets) of patches of that colorant, one on white, one on grey and one on black. Each set of patches goes from 0% to 100% ink coverage (dot percentage in the preferred embodiment applicable to offset printing) in steps of 10% increments. The three sets of patches are shown in FIG. 4 as patches 403-0 though 403-100, 409-0 through 409-100, and 413-0 through 413-100, respectively. One now determines the three spectral parameters for the basic colorant. In one embodiment, one uses Eqns. (4a–4e) as above. Alternatively, one can use a best fit numerical technique for estimating the spectral reflectance of the colorants, as described above in Eqns. (3a–3c) for a single colorant case. Again, preferably, the conjugate directions numerical technique is used, and other numerical techniques may be used as would be clear to one of ordinary skill in the art. Several error functions may be used in the best fit technique, as described above, and as would be clear to those of ordinary skill in the art. For coverage percentages (e.g., dot percentages) which were not measured, in one embodiment, one determines the reflection spectra for the prints on white, on grey and on black by interpolating between the reflection spectra of the dot percentages that were measured. Out of these calculated reflection spectra one can then calculate the colorant parameters as described above for the single colorant. In another embodiment, one determines the spectral parameters of the colorant for any non-measured required coverage percentage by interpolating between the spectral parameters of the colorant for the coverage percentages which were measured.

Thus for the simple case of a derived colorant being one-to-one with a basic colorant, one obtains for that basic colorant three spectral functions, $\alpha(p,\lambda)$, $\mu(p,\lambda)$, and $S(p,\lambda)$, where p is the coverage percentage (e.g., dot percentage) of the colorant. An important property is that the three parameters are essentially invariant with respect to the substrate color (ie., substrate spectral characteristics) for any particular substrate type.

The more complex case is when there is not a one-to-one relationship between the derived colorant and any one of the basic colorants. That is, the derived colorant for printing on substrates of the substrate type simply is in the gamut spanned by the selected basic colorants for printing on substrates of the substrate type. In this case, a derived colorant is made of the basic colorants or has the same color characteristics as a colorant obtained from the basic colorants by using a recipe, that is, by mixing the basic colorants at a certain concentration, denoted $C_i$, with i=1, . . . , n, for the case of n basic colorants. Note that typically, the basic colorants would be applicable only for one type of printing on a particular type of substrate. Using the well known one-constant Kubelka-Munk theory (see, for example, D. B. Judd and G. Wyszecki, *Color in Business, Science, and Industry,* New York: Wiley-Interscience, pp. 420–426, 1975), one can express the Kubelka-Munk constant and the color spectrum of a print with colorant coverage p % of a particular derived colorant using the following two relationships:

$$\left(\frac{K}{S}\right)_p(\lambda) = \left(\frac{K}{S}\right)_{1p}(\lambda, c_1) + \qquad \text{Eqn. (6a)}$$
$$\left(\frac{K}{S}\right)_{2p}(\lambda, c_2) + \ldots + \left(\frac{K}{S}\right)_{np}(\lambda, c_n) + \left(\frac{K}{S}\right)_{substr}(\lambda)$$

$$\left(\frac{K}{S}\right)_{substrate} = \frac{(1 - R_{substrate}(\lambda))^2}{2 R_{substrate}(\lambda)}, \qquad \text{Eqn. (6b)}$$

and $$\left(\frac{K}{S}\right)_{ip}(\lambda) = \frac{(1 - R_{ip}(\lambda))^2}{2 R_{ip}(\lambda)} - \left(\frac{K}{S}\right)_{substrate}(\lambda), \qquad \text{Eqn. (7)}$$

where $R_{ip}(\lambda)$ is the reflection spectrum of basic colorant i with coverage percentage p and $R_{substrate}(\lambda)$ is the spectrum of the substrate. The inverse of Eqn. (7) is $$R_{ip}(\lambda) = 1 + \left(\frac{K}{S}\right)_{ip}(\lambda) + \left(\frac{K}{S}\right)_{substrate}(\lambda) -$$
$$\sqrt{\left(\left(\frac{K}{S}\right)_{ip}(\lambda) + \left(\frac{K}{S}\right)_{substrate}(\lambda)\right) * \left[\left(\frac{K}{S}\right)_{ip}(\lambda) + \left(\frac{K}{S}\right)_{substrate}(\lambda) + 2\right]}.$$

Each of the $(K/S)_{ip}(\lambda)$ values are usually concentration ($c_i$) dependent and coverage percentage p dependent, as indicated by the notation $(K/S)_{ip}(\lambda, c_i)$. In one embodiment of the method of the present invention, one makes a set dilutions of each basic colorant with a dilutant suitable for the set of basic colorants. In the preferred embodiment of using the twelve basic colors from the "CROMALIN" company for the basic colorants, one makes six dilutions of each basic colorant with the "CROMALIN" brand color "transparent white." The six dilutions are of 100%, 50%, 25%, 12%, 6% and 3%, respectively, of each basic colorant. Each such dilution is a colorant that can be characterized using the first part of the techniques described above for the single colorant description. In the preferred embodiment described herein with three-parameter characterization, this means that one makes (e.g., one prints in the preferred embodiment) gradation steps of each dilution of each basic colorant on three different backgrounds, a lightly colored, medium colored, and darkly colored substrate of the same type, lightly colored, medium colored, and darkly colored called white, grey and black, respectively. Again, see FIG. 4. The grey and black can be grey and black substrates or obtained by printing on a white substrate with grey and black colorants, or by printing a medium halftone screen and a dark halftone screen using black colorant, for the case of offset printing using halftone. In the preferred embodiment, the latter approach is used. That is, one first makes (e.g., one prints in the preferred embodiment) strips of 100% black, 50% black (i.e., grey) and 0% black (ie., white), shown as areas 411, 407, and 405, respectively. For each dilution of each basic colorant, one prints three rasters (i.e., sets) of patches of that dilution of that colorant, one on white, one on grey and one on black. Each set of patches goes from 0% to 100% ink coverage (dot percentage in the preferred embodiment applicable to offset printing) in steps of 10% increments. The three sets of patches are shown in FIG. 4 as patches 403-0 though 403-100, 409-0 through 409-100, and 413-0 through 413-100, respectively. In the preferred embodiment, there are 33 patches of 6 dilutions of 12 basic inks.

One now measures the spectrum of each patch. That is, one obtains $R_{piw}(\lambda)$, $R_{pig}(\lambda)$, $R_{pik}(\lambda)$, $R_w(\lambda)$, $R_g(\lambda)$, $R_k(\lambda)$ for each dilution of each basic colorant for the printed p values. Using Eqn. (7), one now determines the K/S value for each of the patches. Thus, for each basic colorant, one has the K/S value at six concentrations (the dilution values) at the 11 coverage percentages printed (including 0%). A derived colorant of interest is specified by its recipe $(c_1, \ldots, c_n)$ for the selected basic colorants. Based on this, one now interpolates in concentration to obtain for each of the printed colorant coverage percentages the values of K/S of each of the basic colorants at the appropriate concentration for that basic colorant, c; for the i'th basic colorant, $i=1, \ldots, n$. Linear interpolation is used in the preferred embodiment. By using Eqn. (6b) on measured $R_w(\lambda)$, $R_g(\lambda)$, and $R_k(\lambda)$, one also has the K/S values of the background substrates, so one now applies Eqn. (6a) to obtain the K/S value for the derived colorant for each of the coverage percentages that were printed with basic colorants on each of the three substrates. Using the inverse of Eqn. (7), one now determines the spectra that would result if the derived colorant would have been printed with a number of gradation steps on three different backgrounds.

Thus by using the recipe (set of $c_1$), one has the calculated reflection spectra for the derived colorant printed on the three background substrates at the set of coverage percentages p at which the dilutions of the basic colorants were printed. That is, one has six calculated spectra: $R_{piw}(\lambda)$, $R_{pig}(\lambda)$, $R_{pik}(\lambda)$, $R_w(\lambda)$, $R_g(\lambda)$, $R_k(\lambda)$. From these six calculated spectra, one determines the three colorant parameters of the derived color in exactly the same way as done in the single colorant case. In one embodiment, one uses Eqns. (4a–4e) as above. Alternatively, one can use a best fit numerical technique for estimating the spectral reflectance of the colorants, as described above in Eqns. (3a–3c) for a single colorant case. For coverage percentages (e.g., dot percentages) not printed, and thus for which no spectra are available, in one embodiment, one determines the reflection spectra for the prints on white, on grey and on black by interpolating between the reflection spectra of the coverage percentages that are available. Out of these calculated reflection spectra one can then calculate the colorant parameters as described above for a single colorant. In another embodiment, one determines the spectral parameters of the derived colorant for any non-measured required coverage percentage by interpolating between the spectral parameters of the derived colorant for the coverage percentages which were measured.

In an alternate embodiment, rather than the one-parameter Kubelka-Munk theory being used, the two-parameter is used. How to modify the step of determining the spectra of overprints of the derived ink from the recipe and from measurements of prints of dilutions of the basic colorants would be clear to one of ordinary skill in the art. In yet other alternate embodiments, other theories for mixtures of colorants may be used for this step.

If the recipe, i.e., the set of concentrations $c_i$, $i=1, \ldots, n$, of n basic colorants for any derived colorant for a printing technique on substrates of a particular type is unknown, it is necessary to determine it. Techniques for recipe determination are known in the art. For example, knowing the color of the derived colorant, for example the color of a print on a white substrate of the substrate type of a 100% patch of the derived colorant, obtained, for example from a sample or from data tables, or by measurement, and knowing the color of each of the basic colorants at 100% coverage at a set of dilutions, these colors obtained, for example, by measurement, one can determine the concentrations $c_i$ for $i=1, \ldots, n$ of each of the n basic colorants using a numerical minimization technique that finds the set of concentrations that minimizes the Euclidean distance in CIE Lab space between the target color (the derived colorant patch) and the color calculated using a recipe of basic colorants, the calculation using the colors of the dilutions, some interpolation, and Eqn. (6) and Eqn. (7) of the one-constant Kubelka-Munk theory described above. In the preferred embodiment, the well-known steepest descent technique is used to search for the set of concentrations that minimizes the Euclidean distance in CIE Lab space. Other numerical methods such as conjugate directions, etc., are possible as would be clear to those of ordinary skill in the art. The Euclidean distance in CIE Lab is $$Dist = \sqrt{(L_c - L_t)^2 + (a_c - a_t)^2 + (b_c - b_t)^2}$$

where $(L_c, a_c, b_c)$ and $(L_t, a_t, b_t)$ are the CIE Lab coordinates of the calculated and target colors, respectively. How to calculate CIE-Lab values from a spectrum is well known in the art. Thus, in one aspect of this invention, for any derived colorant, one either knows or one can determine the recipe of that colorant in terms of a set of basic colorants for printing a particular printing technique on any substrate of a substrate type.

The important result is that the colorant parameters of the basic colorants and of any derived colorant are essentially independent of the substrate color for the printing technique for all substrates of a particular type. As a result, one can calculate the color reflection spectrum $R_p(\lambda)$ resulting from printing the derived colorant with parameters $\alpha(p, \lambda)$, $\mu(p, \lambda)$, and $S(p, \lambda)$, with amount of ink (e.g., dot percentage) p on the substrate being considered, for the particular printing technique and for a particular substrate of a particular type having substrate color reflection spectrum $R_{bg}(\lambda)$, using a formula such as Eqn. (5) above.

To predict the color resulting from printing multiple inks consecutively with a certain ink coverage (e.g., dot percentage) on top of each other, the invariance property of the colorant parameters is used. One can regard a substrate with a colorant printed on it as a substrate of the same type, but having a different color, and one can now determine the color spectrum of laying a second colorant over this first colorant. Thus, according to one embodiment of the method of this invention, to predict the color resulting from printing multiple inks consecutively with a certain ink coverage (e.g., dot percentage) on top of each other, the method applies Eqn. (5) repeatedly in the particular printing order. That is, one then applies Eqn. (5) to determine an overprint formed by laying down different colorants in a particular order. One starts with $R_{bg}(\lambda)$ representing the reflectance of the raw substrate, and uses Eqn. (5) to determine as $R_p(\lambda)$, $R_{p_l}(\lambda)$ of $p_1\%$ of the first colorant applied. One now repeats the calculation by substituting for $R_{bg}(\lambda)$ in Eqn. (5) the $R_{p1}(\lambda)$ obtained by laying down the first colorant on the substrate, and calculating a new $R_p(\lambda)$, $R_{p2}(\lambda)$ representing the result of laying down $p_2\%$ of a second colorant. This can be repeated for a number of colorants in different amounts laid on a substrate in different order.

Thus, according to one embodiment of the method of the present invention, by characterizing a small number of basic colorants on one sample of a substrate of a particular type using a particular printing mechanism, one can predict the color appearance of an overprint of several colorants of a large set of colorants on any substrate of any color, the substrate being of the same particular type.

It would be clear to those of ordinary skill in the art that the colorant determining embodiments disclosed herein for the single colorant case are a simple case of the embodiments described herein for a derived colorant. The single colorant, in this case, is the derived colorant to be characterized, and the associated recipe is the trivial recipe of 100% concentration of a single undiluted basic colorant, that basic colorant being the derived colorant itself. In this case, in the embodiments described herein for a derived colorant, in the step of printing using dilutions of basic colorants, one makes prints of the undiluted colorant at the different coverage percentages on the different background colors. Also, the calculating, using the measured spectra and the recipe, of the spectra that would result from printing the derived colorant is trivial—one uses the measured spectra of the colorant for the calculated-according-to-recipe spectra of the derived colorant. It also would be clear to one in the art that any derived colorant may either be characterized by using a recipe and making prints of dilutions of the basic colorants in the recipe, or by characterizing the derived colorant itself directly (the single colorant case, which is the same as the derived colorant case with the colorant the basic colorant at 100% concentration).

Alternate Embodiment Using Overprints of a Colorant

Yet another embodiment describes a method of characterizing a particular colorant by determining the colorant parameters of the particular colorant on a particular substrate type by successively superimposing layers of the colorant on each other. As before, this is applicable to both transmission and reflection imaging, and only the reflection case will be described. How to extend to the case of transmission imaging would be clear to those of ordinary skill in the art. Again, this is applicable to colorants that are characterized by either two parameters or three parameters.

The case of two-parameter colorants is considered first. This embodiment of the method starts by printing a set of patches of p % of the colorant on the substrate which is assumed to have reflection spectrum $R_{bg}(\lambda)$, again for p=10, 20, ..., 100. One measures the resulting spectra $R_{1p}(\lambda)$ for all these patches. For the case of characterizing the colorant by two colorant parameters, $\alpha_p(\lambda)$ and $\mu_p(\lambda)$, the resulting reflection $R_{1p}(\lambda)$ can be written as:

$$R_{1p}(\lambda)=(1-\alpha_p(\lambda))*R_{bg}(\lambda)^{\mu p(\lambda)}. \qquad \text{Eqn. (8)}$$

One now prints another set of layers of the same colorant with the same set of p % values on top. One measures the resulting spectra $R_{2p}(\lambda)$ for all these patches. The resulting reflection $R_{2p}(\lambda)$ can be written as:

$$R_{2p}(\lambda)=(1-\alpha_p(\lambda)[(1-\alpha_p(\lambda))*R_{bg}(\lambda)^{\mu p(\lambda)}]^{\mu p(\lambda)}. \qquad \text{Eqn. (9)}$$

One now has for each wavelength $\lambda$ two equations, Eqn. (8) and Eqn. (9) with two unknowns, $\alpha_p(\lambda)$ and $\mu_p(\lambda)$. In the preferred embodiments, 36 wavelengths are used: 380 nm, 390 nm, 400 nm, ..., 720 nm, and 730 nm. These unknowns are now determined, preferably using a standard conjugate directions technique for each wavelength for each p % value. In particular, one searches for the $\alpha$ and $\mu$ so that the square of the differences between calculated and measured values of $R_{1p}$, $R_{2p}$ is minimal. For p values that are not printed and measured, as before, interpolation is used.

One of course could modify the method by printing more than two layers of p % on top of one another and numerically determine the parameters $\alpha_p(\lambda)$ and $\mu_p(\lambda)$, for example by numerically minimizing some cost function, for example a weighted sum of the squares of the differences between calculated and measured reflection spectra.

For the case of characterizing the colorant by three colorant parameters, $\alpha_p(\lambda)$, $\mu_p(\lambda)$, and $S_p(\lambda)$, one prints three successive layers of sets of patches, each set for p % colorant coverage for p=10, 20, ..., 100. The corresponding three resulting reflection $R_{1p}(\lambda)$, $R_{2p}(\lambda)$, and $R_{3p}(\lambda)$ are measured for all the patches. The spectra can be written as:

$$R_{1p}(\lambda)=(1-\alpha_p(\lambda))*R_{bg}(\lambda)^{\mu p(\lambda)}+S_p(\lambda) \qquad \text{Eqn. (10)}$$

$$R_{2p}(\lambda)=(1-\alpha_p))[(1-\alpha_p(\lambda))*R_{bg}(\lambda)^{\mu p(\lambda)}+S_p(\lambda)]^{\mu p(\lambda)}+S_p(\lambda) \qquad \text{Eqn. (11)}$$

$$P_{3p}(\lambda)=(1-\alpha_p(\lambda))[(1-\alpha_p(\lambda))[(1-\alpha_p(\lambda))*R_{bg}(\lambda)^{\mu p(\lambda)}+S_p(\lambda)]^{\mu p(\lambda)}+S_p(\lambda)]^{\mu p(\lambda)}+S_p(\lambda) \qquad \text{Eqn. (12)}$$

Again, one now has for each wavelength for each coverage percentage value p % three equations with three unknowns, $\alpha_p(\lambda)$, $\mu_p(\lambda)$ and $S_p(\lambda)$. Again, in the preferred embodiments, 36 wavelengths are used: 380 nm, 390 nm, 400 nm, ..., 720 nm, and 730 nm. These unknowns are now determined preferably using a standard conjugate directions technique. For p values that are not printed and measured, as before, interpolation is used.

While this embodiment is described in terms of reflective imaging, the method extends in a straightforward manner to transmission imaging as would be clear to one of ordinary skill in the art.

As would be clear to those of ordinary skill in the art, one may implement this embodiment by making a single set of printed patches, measuring that set, then making the first overprint over the same set, and measuring the "double" printed patches, then, in the case of three parameters, making one more overprint and measuring the "triple" printed patches. All three sets of patches are then on the same part of the same single substrate. Alternatively, one can make the set of single prints, and the set of double prints, and, if required, the set of triple prints or more separately, on the same or on different substrates of the same color, and measure the resulting two (or three or more) sets. In either case, each set can be considered a set of patches of overprints at different coverage percentage on two (or three or more) substrates, where in some implementations, the two (or three or more) substrates are in fact the same substrate printed to provide different background colors.

If one considers one generalized aspect of the method of the present invention as making enough measurements at each coverage percentage as needed to determine the $n_p$ colorant parameters, then the above described embodiment in the section herein entitled "The single colorant case" of printing on $n_p$ different backgrounds and the just described embodiment of overprinting patches $n_p$ times at each coverage percentage can be considered as special cases of the same general embodiment of the method of the present invention. In each case, at least $n_p$ sets of patches are printed, each set of patches at a set of coverage percentages on substrates of the same substrate type, and the at least $n_p$ patches at any one coverage percentage are printed on backgrounds of at least $n_p$ different background colors. In the embodiment of printing on $n_p$ substrate colors, preferably white, grey and, in the case $n_p=3$, black, all the patches in one set are printed on the same background, and there are two (or three) different backgrounds, while in the just described embodiment of overprinting patches, the $n_p$ patches at any one coverage percentage are printed on a light colored substrate, a light colored substrate with one overprint of the patch at the one percentage coverage, and, for the case $n_p=3$, a third background of a light colored substrate with two overprints of the patch at the one percentage coverage.

Alternate Embodiment Using Test Charts

Yet another embodiment involves determining the colorant parameters necessary for predicting the color appearance of any overprints in a print process which involves overprinting a number of colorants (e.g., inks) using classical test charts. As before this is applicable to both transmission and reflection imaging, and only the reflection case will be described. How to extend to the case of transmission imaging would be clear to those of ordinary skill in the art.

Classical test charts are built as follows. Considering the case of first laying a first colorant on a substrate, and then laying a second, third, etc., colorant on top of the previous layer, a number of patches of different coverage percentages of the first colorant is printed on the substrate. For the second colorant, a number of coverage percentages varying from 0% to 100% is printed on each of the coverage percentages of the first colorant as well as on the raw substrate. For the third colorant, a number of raster percentages varying from 0% to 100% is printed on each of the coverage percentages of the first colorant, on each of the coverage percentages of the second colorant, and on all combinations of the first and second colorants. The process thus continues for all other colorants. Clearly a large number of different patches is involved. It turns out that only a small subset of all the possible color patches in the test chart is enough to determine all colorant parameters necessary to calculate all possible overprints for this printing process. In practice, it was found that only three amounts of colorant coverage, corresponding to a lightly colored, a medium colored, and a dark colored patch need to be overprinted, and that a single overprint over the first color to be laid on the substrate is sufficient for characterizing any colorant other than the first colorant to be laid on the substrate. In addition, that first colorant to be laid on the substrate need not be completely characterized as it will never be printed over any other colorant, it will only be printed on the raw substrate.

Consider for example a common cyan, magenta, yellow and black (CMYK) ink printing process, say an offset printing process where the different coverage percentages are obtained by halftoning with different dot percentages. A classical test chart as described above is printed with the patches being from 0% to 100% dot percentage, in steps of 10% dot percentage. A full test chart would involve more than fourteen thousand patches for four color printing. It turns out that only a small subset of all the possible color patches in the test chart is enough to determine all colorant parameters necessary to calculate all possible overprints for this printing process. In the embodiment described herein, three amounts of colorant coverage, corresponding to a lightly colored, a medium colored, and a dark colored patch can be overprinted, and a single overprint over the first color to be laid on the substrate is used for characterizing a colorant other than the first colorant to be laid on the substrate.

Consider a print of different coverage percentages varying from 0% to 100% on the bare substrate. In typical offset printing, as an example, cyan is the first ink printed, that is, all other inks are printed on top of cyan, and thus cyan will never be printed on top of any of the other inks. Thus there is no need for determining the colorant parameters for cyan; one only needs to know how cyan behaves for different coverage percentages on the substrate. One measures the cyan-only patches on the test chart for the eleven coverage percentages 0%, 10%, ..., 100%, and interpolates for intermediate coverage percentages (e.g., dot percentages for offset printing) that have not been measured.

One now prints patches of different coverage percentages of magenta on 100% cyan, on 50% cyan and on 0% cyan. For each printed coverage percentage p % of magenta, one can write:

$$R_{p100\%C}(\lambda)=(-\alpha_p(\lambda))*R_{100\%C}(\lambda)^{\mu_p(\lambda)}+S_p(\lambda), \qquad \text{Eqn. (13)}$$

$$R_{p50\%C}(\lambda)=(1-\alpha_p(\lambda))*R_{50\%C}(\lambda)^{\mu_p(\lambda)}+S_p(\lambda), \text{ and} \qquad \text{Eqn. (14)}$$

$$R_{0\%C}(\lambda)=(1-\alpha_p(\lambda))*R_{0\%C}(\lambda)^{\mu_p(\lambda)}+S_p(\lambda). \qquad \text{Eqn. (15)}$$

By measuring $R_{p100\%C}(\lambda)$, $R_{p50\%C}(\lambda)$ $R_{p0\%C}(\lambda)$, $R_{100\%C}(\lambda)$, $R_{50\%C}(\lambda)$ and $R_{0\%C}(\lambda)$, one uses a numerical technique, conjugate directions in the preferred embodiment, to solve for $\alpha_p(\lambda)$, $\mu_p(\lambda)$, and $S_p(\lambda)$, the colorant parameters for the magenta ink. As would be clear to those of ordinary skill in the art, other implementations are possible within the scope of this aspect of the invention. For example, for any p, one can use more prints of the same p % magenta on more background colors of some other percentages, say x % of cyan, and use the same minimization technique to determine $\alpha_p(\lambda)$, $\mu_p(\lambda)$ and $S_p(\lambda)$.

Prints of different coverage percentages of yellow on 100% cyan, on 50% cyan and on 0% cyan are now made. For each printed coverage percentage p % of yellow, the same equations Eqn. (13), Eqn. (14), and Eqn. (15) above apply, where $\alpha_p(\lambda)$, $\mu_p(\lambda)$ and $S_p(\lambda)$ are now the colorant parameters for the yellow ink. Again, by measuring $R_{100\%C}(\lambda)$, $R_{p50\%C}(\lambda)$, $R_{p0\%C}(\lambda)$, $R_{100\%C}(\lambda)$, $R_{50\%C}(\lambda)$ and $R_{0\%C}(\lambda)$ one uses a numerical technique to solve for the colorant parameters $\alpha_p(\lambda)$, $\mu_p(\lambda)$ and $S_p(\lambda)$ for the yellow ink.

To characterize the black, prints of different coverage percentages of black are made on 100% cyan, on 50% cyan and on 0% cyan. The three colorant parameters of black are then calculated in the same way as we described above for the magenta and yellow inks.

Alternatively, the parameters of the yellow colorant can be determined by printing different dot percentages of yellow on 100% magenta, on 50% magenta and on 0% magenta. In this case, for each printed raster percentage p of yellow, the applicable equations are:

$$R_{p100\%M}(80)=(1-\alpha_p(\lambda))*R_{100\%M}(\lambda)^{\mu_p(\lambda)}+S_p(\lambda), \qquad \text{Eqn. (16)}$$

$$R_{p50\%M}(\lambda)=(1-\alpha_p(\lambda))*R_{50\%M}(\lambda)^{\mu_p(\lambda)}+S_p(\lambda), \text{ and} \qquad \text{Eqn. (17)}$$

$$R_{p0\%M}(\lambda)=(1-\alpha_p(\lambda))*R_{0\%M}(\lambda)^{\mu_p(\lambda)}+S_p(\lambda). \qquad \text{Eqn. (18)}$$

Again, by measuring $R_{p100\%M}$, $R_{p50\%M}$, $R_{p0\%M}$, $R_{100\%M}$, $R_{50\%M}$, and $R_{0\%M}$, one can numerically determine $\alpha_p(\lambda)$, $\mu_p(\lambda)$ and $S_p(\lambda)$ for the yellow colorant by solving Eqns. (16)–(18).

Alternate embodiments of the method of the present invention for determining the parameters for the black colorant include producing prints of different coverage percentages of black on 100% magenta, on 50% magenta and on 0% magenta. Another alternative includes printing different coverage percentages of black on 100% yellow, on 50% yellow and on 0% yellow. Also within the scope of the present invention is determining the black colorant parameters by printing different coverage percentages of black on a light, a medium dark and a dark color appearing in the test chart. How to modify the above equations to determine the parameters using these different embodiments would be clear to those of ordinary skill in the art.

An Apparatus for Determining Colorant Overprints

Another aspect of the present invention is an apparatus for determining the spectrum of colorant overprints. As before this is applicable to both transmittance and reflection imaging, and only the reflection case will be described. How to extend to the case of transmission imaging would be clear to those of ordinary skill in the art.

Figure 6:
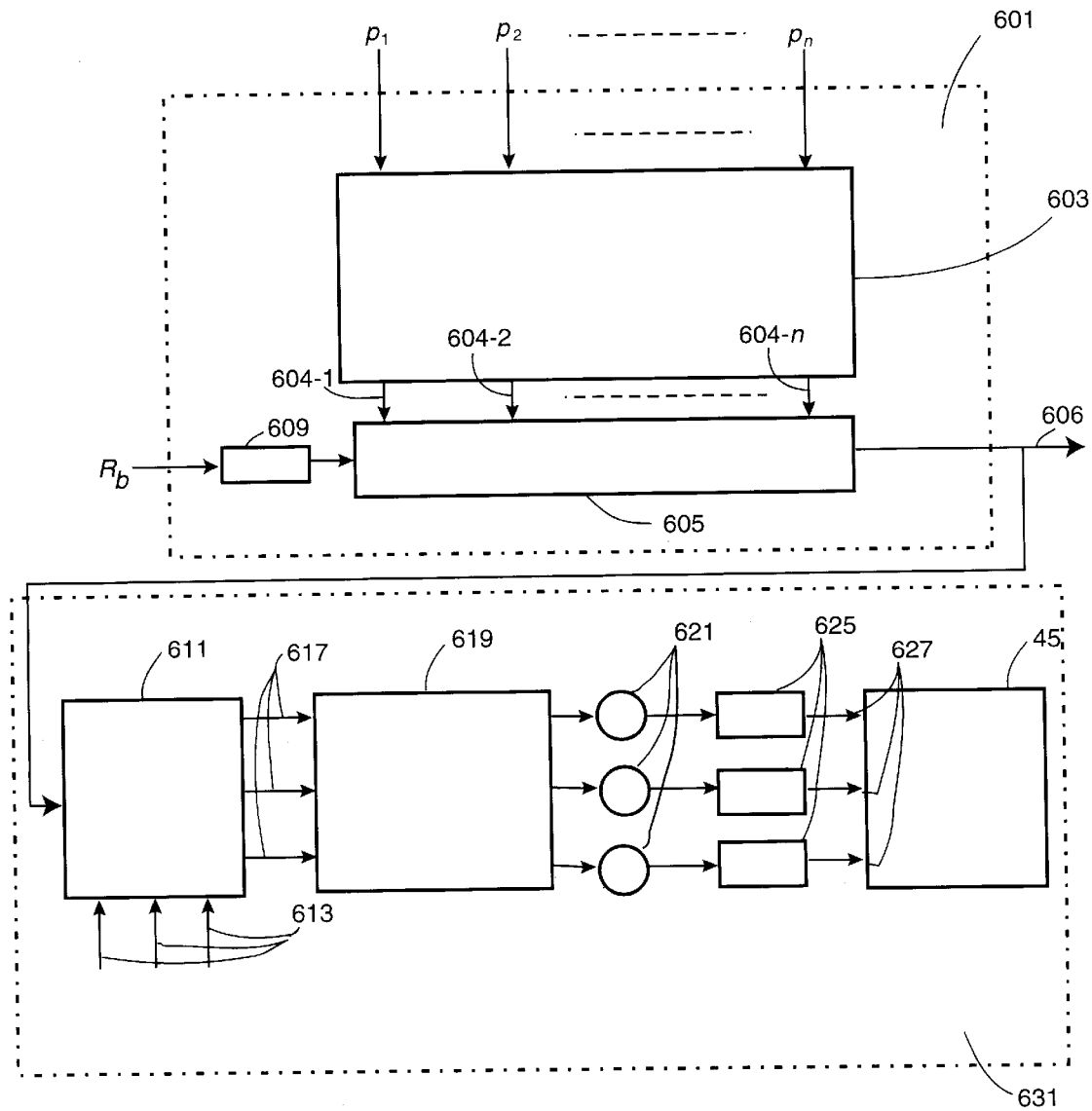
FIG. 6 shows an apparatus for determining the spectral color parameters of colorants and for determining the color spectrum of overprints according to an embodiment of the invention. Included in this diagram is an apparatus for using the color spectrum of overprints to simulate color appearance on a CRT display.

The preferred embodiment of the apparatus of the present invention is shown as item 601 in FIG. 6. An example will be followed of how apparatus 601 calculates the color spectrum of an overprint of n colorants with respective coverage percentages $p_1, \ldots, p_n$ on a background with background reflectance $R_b(\lambda)$. It is assumed that each of the colorants has been characterized, for example using one of the embodiments of the method of the present invention described above. That is, each colorant has been characterized by either two spectral parameters, three spectral parameters or more than three spectral parameters. That is, each colorant has a set of $n_p$ colorant parameters, where $n_p$ is at least 2.

Apparatus 601 has as input the reflection spectrum of the background $R_b(\lambda)$ and n signals representing the n colorant coverage amounts (dot percentages of inks for the case of offset printing) denoted $p_1, \ldots, p_n$, respectively. In the preferred embodiment, the spectrum is quantized into a finite number, $n_1=36$, of wavelengths $\lambda_1, \lambda_2, \ldots, \lambda_{n_1}$, so that $R_b(\lambda)$ consists of the 36 samples of the spectrum at the 36 wavelengths. Coupled to the spectrum input is a first memory 609 for storing the $n_l$ samples of the background spectrum $R_b(\lambda)$ at the $n_1$ wavelengths. Also included is a logic unit 603 coupled to the n inputs which determines, as n sets of outputs, denoted 604-1, 604-2, . . . , 604-n, respectively, the values of the colorant parameters (the functions $\alpha(p, \lambda)$ and $\mu(p, \lambda)$ in the two-parameter case) for the n input p values $p_1, \ldots, p_n$, respectively, for all $n_1$ values of $\lambda$. These n outputs 604-1, 604-2, . . . , 604-n are coupled to a combiner unit 605 as inputs to 605. Combiner unit 605 also has a second input which is coupled to first memory 609 containing the background spectrum input $R_b(\lambda)$. The output 606 of combiner unit 605 is the color spectrum at the $n_1$ wavelengths resulting from overprinting the n colorants at coverage percentage $p_1, \ldots, p_n$, respectively, when laid over the substrate. Combiner unit 605 sequentially uses for instance Eqn. (2) for the case of two-parameter-characterized colorants, or Eqn. (5) for the three-parameter case.

One implementation of logic unit 603 is a direct table lookup mechanism which includes a second memory, in particular RAM, for storage of the table. This mechanism is used for all possible input values of $p_1, \ldots, p_n$, for all wavelengths $n_1$ and for all colorant parameters. For the case of 8-bit quantities for $p_1, \ldots, p_n$, a reasonable amount of memory (e.g., RAM) is required to store the colorant parameters.

Figure 7:
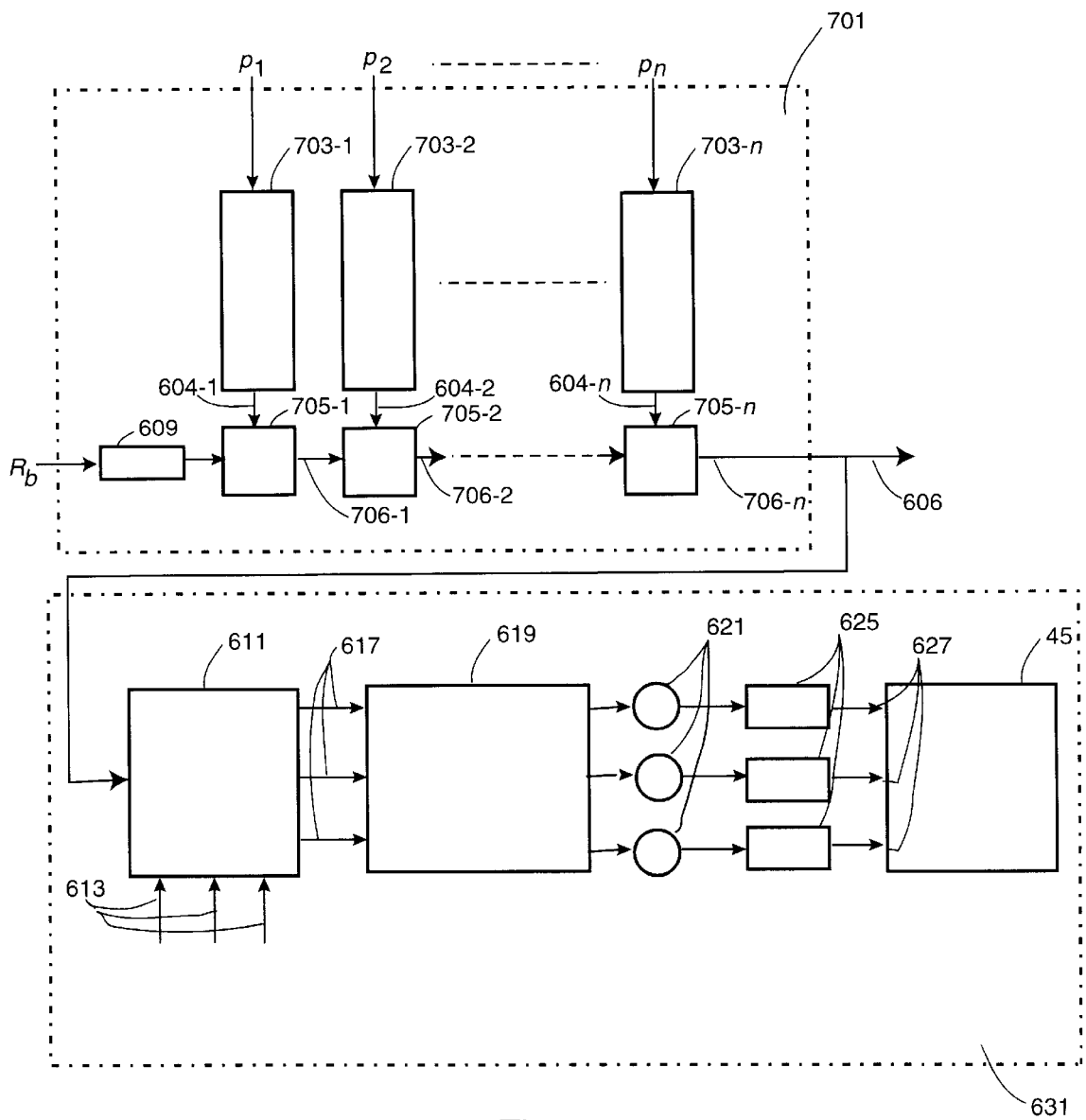
FIG. 7 shows one particular embodiment of the apparatus of FIG. 6 for determining the spectral color parameters of colorants and for determining the color spectrum of overprints. Included in this diagram is the apparatus from FIG. 6 for using the color spectrum of overprints to simulate color appearance on a CRT display.

An alternate embodiment of logic unit 603 as n interpolation units is shown in FIG. 7, which also shows one preferred embodiment of combiner unit 605 as n arithmetic units. First consider logic unit 603 implemented as n interpolation units, denoted 703-1, 703-2, . . . , 703-n, respectively, to which are coupled the n coverage percentage inputs. Each interpolation unit, say the i'th, $i=1, \ldots, n$, corresponds to one of the colorants, in particular the i'th colorant, and thus has coupled to it the input coverage percentage $p_i$. In one implementation, each interpolation unit includes $n_l * n_p$ interpolators, and contains the colorant parameters for its associated colorant for a small set of values of p. For example, in the case of using two parameters per colorant, in the preferred embodiment, each interpolation unit 703-1, 703-2, . . . , 703-n contains the values for the associated colorant of $\alpha_p(\lambda)$ and $\mu_p(\lambda)$ for all $n_l$ values of $\lambda$ for 11 values of p, $p=0, 10, \ldots$, and 100, respectively. By interpolation between values of p for which the parameters are stored, each interpolation unit 703-i, $i=1, \ldots, n$, determines the parameters (the functions $\alpha(p, \lambda)$ and $\mu(p, \lambda)$ in the two-parameter case) for its respective input p value $p_i$, for all $n_l$ values of $\lambda$. That is, each coverage percentage $p_i$, $i=1, \ldots, n$ at the input side is fed into a corresponding interpolation unit 703-i of $(n_p * n_l)$ that calculates as output 604-i the values at all $n_l$ wavelengths of the $n_p$ colorant parameters of the corresponding i'th colorant at that coverage percentage $p_i$.

The particular embodiment of combiner unit 605 shown in FIG. 7 is now described. The outputs 604-1, 604-2, . . . , 604-n of either the n interpolation units 703-1, 703-2, . . . , 703-n, respectively, of FIG. 7, or the lookup table mechanism in one alternate embodiment of 603, or some other implementation of logic unit 603, are n sets of $n_p$ spectral colorant parameters at $p=p_1, \ldots, p_n$, respectively. These outputs are coupled to n arithmetic units 705-1, 705-2, . . . , 705-n, each arithmetic unit also having a second input. The second input of the first arithmetic unit 705-1 is coupled to first memory 609 containing the background spectrum input $R_b(\lambda)$. The second input of each subsequent arithmetic unit is coupled to the output of the previous arithmetic unit. The output of each arithmetic unit 705-i $i=1, \ldots, n$, is the color spectrum of the colorant of coverage percentage $p_i$ when laid over the substrate only (for $i=1$) or when laid over the substrate with all the colorants $1, \ldots, i-1$ laid in order, for other values if i. Each arithmetic unit 705-i, $i=1, \ldots, n$, uses for instance Eqn. (2) for the case of two-parameter-characterized colorants, or Eqn. (5) for the three-parameter case. In one embodiment, each arithmetic unit 705-i, $i=1, \ldots, n$, includes: a) an exponentiation unit which, for each wavelength, exponentiates the value of the signal of the second input by the first colorant parameter from the first input, that is, determines (the second input)(the first colorant parameter of the first input), where  is exponentiation; b) a multiplication unit which multiplies the result of the exponentiation by the value of the second colorant parameter from the first input; and c) an adder unit which adds for each wavelength the value of the third colorant parameter (if any) from the first input to the result of the multiplication and exponentiation. Thus, arithmetic unit 705-1 calculates the reflectance spectrum of the print of colorant 1 at raster percentage $p_1$ on the substrate with spectrum $R_b$ resulting in a spectral color $R_{b+Color\ 1}(\lambda)$. In arithmetic unit 705-2, the effect of colorant 2 at raster percentage $P_2$ is added by using the same method as arithmetic unit 705-1, but now $R_{b+Color\ 1}(\lambda)$ takes the place of the background color. The final output 706-n is the reflection spectrum 606 of the superimposition of all the colorant layers.

Figure 8:
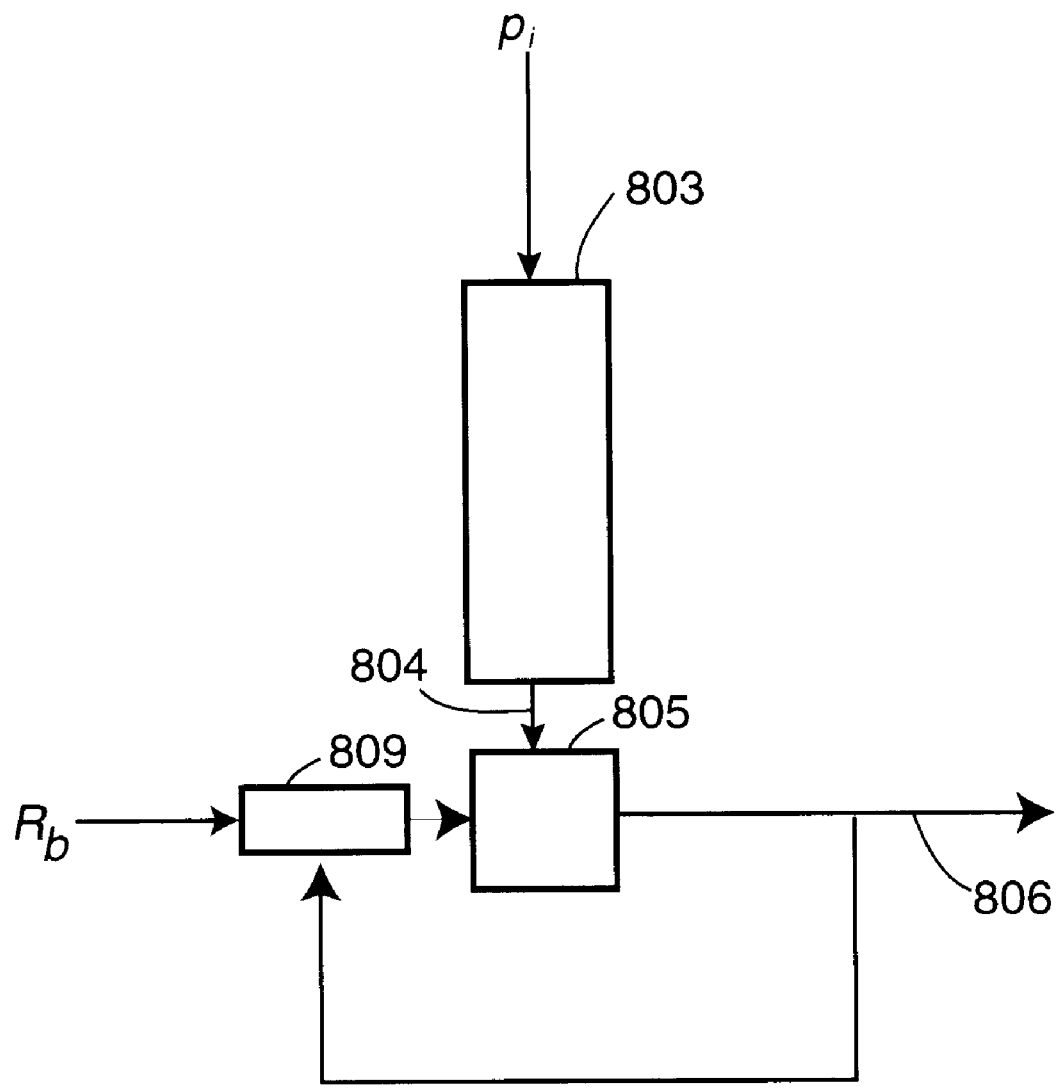
FIG. 8 shows an alternate implementation of the apparatus of FIG. 6 for determining the spectral color parameters of colorants and for determining the color spectrum of overprints according to an embodiment of the invention.

The above embodiment can be thought of as a "parallel" implementation of determining the overprints. In another embodiment, the n interpolation units implementing logic unit 603, and the n arithmetic units implementing combiner unit 605 can be replaced by a single interpolation unit and a single arithmetic unit that operate in a serial manner in n cycles. This is shown in FIG. 8. Interpolation unit 803 has as an input the percentage of a colorant, and accepts as constants the values of the $n_p$ parameters for that colorant at a small number of coverage percentages at $n_l$ wavelengths. The output 804 of the interpolation unit 803 is the set of the values of the $n_p$ parameters for that colorant at the $n_l$ wavelengths for coverage percentage $p_l$. Output 804 is coupled to the first input of arithmetic unit 805. A second input of arithmetic unit 805 is coupled to the output of a storage buffer (a memory) 809 which stores a background spectrum. The output 806 of arithmetic unit 805 is the color spectrum at the $n_l$ wavelengths of the colorant laid over a substrate with the spectrum of the second input of arithmetic unit 805. At initialization, storage buffer 809 accepts as input some spectrum $R_b(\lambda)$. At the end of each cycle, storage buffer 809 accepts as input the output spectrum of arithmetic unit 805 from the previous cycle. The serial device operates as follows. In the first cycle, interpolation unit 803 is loaded with the values of the $n_p$ parameters for the first colorant at $n_l$ wavelengths for the small set of coverage percentages, and the input of interpolation unit 803 is coupled with the number $p_1$. The output 804 of the interpolation unit 803 is then the value of the parameters of the first colorant at coverage percentage $p_1$. This is coupled to the first input of arithmetic unit 805. Storage buffer 809 is first loaded with the value of the substrate spectrum $R_b(\lambda)$. Thus at the end of the first cycle, the output 806 of the arithmetic unit is the spectrum of the substrate with a single overprint of the first colorant at coverage $p_1$. This is coupled to storage buffer 809. In each subsequent cycle, for example, the i'th cycle, i=2, . . . , n, the set of interpolators is loaded with the values of the $n_p$ parameters at the small number of coverage percentages for the i'th colorant at $n_l$ wavelengths, and has as input the coverage percentage $p_l$. Storage buffer 809 contains the output spectrum corresponding to overprints of the of the (i-1) previous colorants. Thus, at the end of n cycles, the output 806 of arithmetic unit 805 is the spectrum 606 of the n overprints.

Not shown in apparatus 601 of FIG. 6, 701 of FIG. 7, and the apparatus of FIG. 8 are the control units necessary to operate the various blocks. Including such control units would be clear to those of ordinary skill in the art. Each of the blocks in apparatus 601 of FIG. 6, 701 of FIG. 7, and the apparatus of FIG. 8 may be implemented in various ways. For example, each may be implemented as a set of computer instructions operating on computer system 10. Alternatively, some or all blocks may be built using special hardware, for example using digital signal processor ("DSP") devices, or using programmable logic, or using special purpose logic, for example, one or more application specific integrated circuits ("ASICs"). It would be clear to those in the art that many ways of implementing the apparatus is possible, and how to design such specific implementations would be clear to those of ordinary skill in the art.

A feature of the embodiments of the apparatus described herein is that the colorants have been characterized according to the method of the invention for characterizing colorants. As described above, characterizing includes using a relationship relating the spectrum of a print of the colorant at a coverage percentage of the colorant to the spectrum of the background color and the colorant parameters at that coverage percentage, the relationship using the key property of the colorant parameters that they are substantially independent of the color of the substrate for a particular substrate type. The particular definition of the colorants used depends on the particular relationship used. In the preferred embodiments described herein, for the two-parameter case, the relationship takes the form of Eqn. (2), while for the three parameter case, the relationship takes the form of Eqn. (5). Other embodiments are possible within the scope of the invention that use a different relationship for the relationship relating the spectrum of the print at a coverage percentage of the colorant to the spectrum of the background color and the colorant parameters at that coverage percentage, thus providing an alternate set of parameters. In particular, the way logic unit 603 and combiner unit 605 would need to change for any such alternate set of parameters, and how to modify the embodiments described herein in such a case would be clear to one of ordinary skill in the art.

Method and Apparatus of Simulating Prints on a Proof Printer or on a Display

Another aspect of the invention is a method and apparatus for determining color values, for example CIE XYZ values or CIE-Lab or other color values of an overprint of n colorants on a substrate using the colorant parameters determined according to the above aspects of the invention. Yet another aspect is using these color values for simulating the visual appearance of an overprint of n colorants on a substrate on a display, for example, CRT monitor 45 of display subsystem 22 of computer system 10, or on a printer, for example, a proof printer. The emphasis of the description herein is on an apparatus for such determination, and it would be clear to those of ordinary skill in the art from this description how to implement the conversions and simulations as a method.

Additional apparatus for another aspect of the invention is shown as apparatus 631 in FIGS. 6 and 7. One may apply one or more of the embodiments of the method and apparatus of the present invention to determining color values, for example CIE XYZ values of a overprint of n colorants on a substrate. Similarly, CIE-Lab or other values may in alternatively be determined.

Additional apparatus for these aspects of the invention is shown as apparatus 631 in FIGS. 6 and 7. One may apply one or more of the embodiments of the method and apparatus of the present invention to determining color values, for example CIE XYZ values of an overprint of n colorants on a substrate. Similarly, CIE-Lab or other values may alternatively be determined. In another aspect of the present invention, these CIE-XYZ values can then be converted to RGB values to produce RGB signals to drive a color monitor, for example, CRT monitor 45 of display subsystem 22 of computer system 10. The image on the CRT is then used as an accurate simulation of the overprint of the n colorants. In FIG. 6, controller and CRT display 631 includes the hardware apparatus for displaying the overprint, and takes as input the reflection spectrum 606 which is the output of apparatus 601. The implementation of apparatus 601 may be as shown in FIG. 6, FIG. 7, or FIG. 8 or may be other alternate implementation. As stated above, these blocks also may be implemented as a set of method steps implemented on a computer such as computer system 10. The spectrum from apparatus 601 or another alternate apparatus is fed into a color values converter, shown as 611. In the preferred embodiment of the apparatus, 3*$n_l$ multiplier adders are used, which have as additional input the CIE illuminant-observer weightings 613. The output 617 is the set of CIE-XYZ values. How to carry out this conversion operation from a spectrum to CIE values is known in the art. The CIE-XYZ values 617 are fed into color coordinate converter, which preferably includes a 3×3 matrix multiplier 619, three adders 621, and three lookup tables 625 with the adder outputs as inputs, the lookup tables for gamma correction to produce the RGB signals 627 which are then fed into CRT monitor 45. How to carry out the transformation of the color coordinate converter from CIE-XYZ to RGB values is known in the art. The resulting image visualized on monitor 45 is a very accurate visualization of the overprint.

In another aspect of the present invention, the CIE-XYZ values 617, or the RGB values from lookup tables 625 may be fed to a multi-dimensional interpolator to determine the device dependent color values of a particular printing device such as a printer. The output of this interpolator can be sent to such a printing device. One practical application is color proofing, where the printing device is a proofing printer. The print resulting from such a printer is then an accurate simulation on the medium of the proofer of the overprint of the n colorants on the original substrate of spectrum $R_b$. How to carry out color conversions from CIE-XYZ values or CIE-Lab values to the device color space of a particular printing device is known in the art.

In one preferred embodiment as a method for simulating the appearance of the overprint of the colorants on a printer, for example a proof printer, the simulation on a printer is a set of computer implemented method steps. These steps can be incorporated in a raster image processor ("RIP") system used to drive the printer.

As would be clear to those of ordinary skill in the art, each of the blocks in apparatus 631 and of the analogous method may be implemented in various ways, for example, as a set of computer instructions operating on computer system 10 or as special hardware which might use one or more DSPs or ASICs.

Again, the above description was mostly for reflection imaging. How to modify the various embodiments of the method and apparatus of the present invention for the case of transmission imaging would be clear to those of ordinary skill in the art.

Although this invention has been described with respect to preferred embodiments, those embodiments are illustrative only. No limitation with respect to the preferred embodiments is intended or should be inferred. It will be observed that numerous variations and modifications may be effected without departing from the true spirit and scope of the novel concept of the invention, and it is intended that the scope of the invention be defined by the claims appended hereto.

What is claimed is:

1. A method for determining respective sets of $n_p$ parameters that spectrally characterize one or more colorants in order to predict the color of an overprint of the colorants printed in an order of printing at a set of respective coverage percentages on a substrate of a substrate type using a printing technique, each of the colorants defined by a respective recipe of one or more basic colorants, the method comprising, for a particular colorant of the colorants:

(a) for each basic colorant of the respective recipe defining the particular colorant:

(i) making a selected number of sets of prints of the basic colorant on said selected number of respective substrates of the same substrate type, a set of prints comprising prints of the basic colorant on the respective substrate at a range of coverage percentages of interest, the selected number of prints at any particular coverage percentage being on backgrounds of said selected number of different background colors, said selected number dependent on $n_p$;

(ii) measuring the spectra of the prints of the selected number of sets of prints and the spectra of each of the different background colors; and (b) determining from the recipe and from the measured spectra, the set of $n_p$ colorant parameters of the particular colorant as a function of the coverage percentage and of wavelength, the colorant parameters substantially independent of the color of the substrate.

2. The method of claim 1 wherein in step (a), the selected number is at least $n_p$, $n_p$ is at least 2 for any non-scattering basic colorant and at least 3 for any scattering basic colorant, and said step (b) essentially uses a relationship relating the spectrum of a print of a selected colorant at a selected coverage percentage of said range of coverage percentages on a base substrate to the spectrum of the base substrate and the set of colorant parameters of the selected colorant at the selected coverage percentage.

3. The method of claim 2 wherein the selected number of respective substrates have different colors and the different background colors are the different substrate colors.

4. The method of claim 2 wherein the at least $n_p$ respective substrates have at least $n_p$ different colors, a first substrate of the at least $n_p$ substrates is a lightly colored substrate, a second substrate of the at least $n_p$ substrates is a medium colored substrate, and for the case $n_p=3$, a third substrate of the at least $n_p$ substrates is a darkly colored substrate, the light color of the first substrate, the medium color of the second substrate, and for the case $n_p=3$, the dark color of the third substrate being at least some of the different colors.

5. The method of claim 4 wherein the medium colored substrate is a greyish substrate, and for the case $n_p=3$, the darkly colored substrate is a blackish substrate.

6. The method of claim 4 wherein the medium colored substrate is the lightly colored substrate printed with a second colorant at a medium coverage percentage, and for the case $n_p=3$, the darkly colored substrate is the lightly colored substrate printed with a second colorant at a high coverage percentage.

7. The method of claim 4 wherein the medium colored substrate is the lightly colored substrate printed with a second colorant at a first coverage percentage, and for the case $n_p=3$, the darkly colored substrate is the lightly colored substrate printed with a third colorant at second coverage percentage.

8. The method of claim 5 wherein said greyish substrate is the light colored substrate printed with a grey colorant, and for the case $n_p=3$, the blackish substrate is the lightly colored substrate printed with a black colorant.

9. The method of claim 5 wherein said greyish substrate is the lightly colored substrate printed with a black colorant at a certain coverage percentage, and for the case $n_p=3$, the blackish substrate is the lightly colored substrate printed with a black colorant at a high coverage percentage.

10. The method of claim 2 wherein in said step (a)(i), making a first set of prints comprises making a set of prints on a first substrate with a first set of coverage percentages;

making a second set of prints comprises making a set of prints with a second set of coverage percentages to produce a first intermediate set, and on the first intermediate set, making a set of prints at a third set of coverage percentages so that the basic colorant is overprinted twice in said second set of prints; and for the case $n_p=3$, making a third set of prints comprises making a set of prints with a fourth set of coverage percentages to produce a second intermediate set, and on the second intermediate set, making another set of prints at a fifth set of coverage percentages to produce a third intermediate set, and on the third intermediate set, making yet another set of prints at a sixth set of coverage percentages so that the basic colorant is overprinted three times in said third set of prints.

11. The method of claim 10 wherein said second set of coverages and said third set of coverages are the same as the first set of coverages so that the basic colorant is overprinted twice at each coverage percentage of the first set of coverage percentages in said second set of prints, and wherein, for the case $n_p=3$, the fourth set of coverage percentages, the fifth set of coverage percentages, and the sixth set of coverage percentages are the same as the first set of coverages so that the basic colorant is overprinted three times at each coverage percentage of the first set of coverage percentages in said third set of prints.

12. The method of claim 11 wherein said first intermediate set is said first set of prints.

13. The method of claim 11 wherein for the case $n_p=3$, said second intermediate set is said second set of prints.

14. The method of claim 12 wherein for the case $n_p=3$, said second intermediate set is said second set of prints.

15. The method of claim 2 wherein step (b) includes using the method of conjugate gradients.

16. The method of claim 4 wherein, for a particular colorant percentage not equal to any of said set of coverage percentages, step (b) includes at said wavelength determining the interpolated values of at least $n_p$ spectra of the particular colorant printed at said particular colorant percentage on the at least $n_p$ sets of prints, using interpolation between measured values of the at least $n_p$ sets of spectra, and determining from said interpolated values the set of $n_p$ colorant parameters for the particular colorant at said particular colorant percentage.

17. The method of claim 4 wherein, for a particular colorant percentage not equal to any of said set of coverage percentages, step (b) includes at said wavelength determining a first set of values of the set of colorant parameters at a first coverage percentage of said set of coverage percentages, the first coverage percentage less than the particular coverage percentage, and a second set of values of the set of colorant parameters at a second coverage percentage of said set of coverage percentages, the second coverage percentage greater than the particular coverage percentage, and determining the set of colorant parameters for the particular colorant at said particular colorant percentage by interpolating between the first set of values and the second set of values.

18. The method of claim 11 wherein, for a particular colorant percentage not equal to any of said set of coverage percentages, step (c) includes at said wavelength determining the interpolated values of at least $n_p$ spectra of the particular colorant printed at said particular colorant percentage on the at least $n_p$ sets of prints, using interpolation between measured values of the at least $n_p$ sets of spectra, and determining from said interpolated values the set of $n_p$ colorant parameters for the particular colorant at said particular colorant percentage.

19. The method of claim 11 wherein, for a particular colorant percentage not equal to any of said set of coverage percentages, step (c) includes at said wavelength determining a first set of values of the set of colorant parameters at a first coverage percentage of said set of coverage percentages, the first coverage percentage less than the particular coverage percentage, and a second set of values of the set of colorant parameters at a second coverage percentage of said set of coverage percentages, the second coverage percentage greater than the particular coverage percentage, and determining the set of colorant parameters for the particular colorant at said particular colorant percentage by interpolating between the first set of values and the second set of values.

20. The method of claim 2 wherein the method includes:

making a set of dilutions of each basic colorant in the recipe;

and repeating step (a) for each dilution of each said basic colorant, in step (b), using said recipe and the measured spectra from the repeating of step (a), determining a set of calculated spectra that would result by producing at least $n_p$ new sets of prints, each new set comprising prints of the colorant at the range of coverage percentages on the at least $n_p$ respective substrates, the at least $n_p$ prints at any particular coverage percentage being on backgrounds of said selected number of different background colors.

21. The method of claim 20 wherein for the particular colorant, each said basic colorant has a corresponding concentration in said recipe and wherein step (b) further comprises determining for each basic colorant from at least some of the spectra measured in step (a)(ii) the Kubelka-Munk coefficient values of said each basic colorant at the corresponding concentration.

22. The method of claim 21 wherein for any basic colorant whose corresponding concentration is not one of said dilutions, said determining the Kubelka-Munk coefficient values includes determining the Kubelka-Munk coefficient values for at least two of said dilutions, and interpolating between the so determined Kubelka-Munk coefficient values for the at least two of said dilutions.

23. The method of claim 20 wherein the selected number of respective substrates have different colors and the different background colors are the different substrate colors.

24. The method of claim 20 wherein the at least $n_p$ respective substrates have at least $n_p$ different colors, a first substrate of the at least $n_p$ substrates is a lightly colored substrate, a second substrate of the at least $n_p$ substrates is a medium colored substrate, and for the case $n_p=3$, a third substrate of the at least $n_p$ substrates is a darkly colored substrate, the light color of the first substrate, the medium color of the second substrate, and for the case $n_p=3$, the dark color of the third substrate being at least some of the different colors.

25. The method of claim 23 wherein the medium colored substrate is a greyish substrate, and for the case $n_p=3$, the darkly colored substrate is a blackish substrate.

26. The method of claim 2 further comprising the step of (c) determining the color spectrum of an overprint of the colorants printed at the set of respective percentages, the method comprising, for each colorant, in the order of the overprinting, calculating the spectrum of the overprint on a selected base substrate using the parameters of said each colorant and the spectrum of the selected base substrate, the selected base substrate for the first printed colorant being the substrate, and the selected base substrate for each successive overprint being the overprint of all the previously printed colorants on the substrate.

27. The method of claim 26 wherein in step (c), determining the color spectrum uses said relationship.

28. The method of claim 20 further comprising the step of
(c) determining the color spectrum of an overprint of the colorants printed on the set of respective percentage, the method comprising, for each colorant, in order of the overprinting, calculating the spectrum of the overprint on a selected base substrate using the parameters of said each colorant and the spectrum of the selected base substrate, the selected base substrate for the first printed colorant being the substrate, and the selected base substrate for each successive overprint being the overprint of all the previously printed colorants on the substrate.

29. The method of claim 28 wherein in step (c), determining the color spectrum uses said relationship.

30. The method of claim 26 further including converting the color spectrum of the overprint of the colorants to a set of color values which describe the color appearance overprint of the colorants.

31. The method of claim 28 further including converting the color spectrum of the overprint of the colorants to a set of color values which describe the color appearance overprint of the colorants.

32. The method of claim 30 further including using said color values to drive a display.

33. The method of claim 31 further including using said color values to drive a display.

34. The method of claim 30 wherein said color values are the device dependent color values for creating said appearance on a printing device.

35. The method of claim 31 wherein said color values are the device dependent color values for creating said appearance on a printing device.

36. The method of claim 2 wherein, denoting a coverage percentage by p, a wavelength by $\lambda$, the set of colorant parameters of the selected colorant at the selected coverage percentage p by $\alpha_p(\lambda)$, $\mu_p(\lambda)$, and for the case $n_p=3$, $S_p(\lambda)$, respectively, the spectrum of the p % print of the selected colorant on the base substrate having a spectrum $R_{bg}(\lambda)$ by $R_p(\lambda)$, said relationship relating $R_p(\lambda)$ to $R_{bg}(\lambda)$ and the set of colorant parameters of the selected colorant for the case $n_p=2$ is approximately $$R_p(\lambda)=(1-\alpha(p, \lambda))*R_{bg}(\lambda)^{\mu(p,\lambda)},$$

and for the case $n_p=3$ is approximately $$R_p(\lambda)=(1-\alpha(p, \lambda))*R_{bg}(\lambda)^{\mu(p,\lambda)}+S(p, \lambda).$$

37. An apparatus for determining the color of an overprint of one or more colorants each colorant printed in an order at a respective coverage percentage on a substrate of a substrate type, each colorant defined by a set of $n_p$ colorant parameters that are a function of the coverage percentage the colorant is printed on, and of wavelength, the colorant parameters substantially independent of the color of the substrate the colorant is printed on, $n_p$ being at least 2 for a non-scattering colorant and at least 3 for a scattering colorant, the set of colorant parameters defined by a relationship relating the spectrum of a print of a selected colorant at a selected coverage percentage on a base substrate to the spectrum of the base substrate and the set of colorant parameters of the selected colorant at the selected coverage percentage, the apparatus comprising:

(a) a first memory for storing a spectrum, said first memory initially storing the spectrum of the substrate;

(b) a logic unit, the logic unit including a set of one or more inputs, the inputs coupled to signals specifying a coverage percentage, a second memory for storing the values of the colorant parameters of at least one of the colorants at a selected set of coverage percentages, a set of one or more multidimensional outputs, each multidimensional output generating the values of the colorant parameters at the coverage percentage of a respective input of the set of inputs, (c) a combiner unit having a first input coupled to the first memory, the combiner unit coupled to said set of outputs of the logic unit for determining as an output the spectrum of an overprint essentially according to the relationship.

38. The apparatus claim 37 wherein the logic unit includes one or more parameter determining mechanisms, each parameter determining mechanism having a coverage input coupled to one of the inputs of the logic unit and a parameter output coupled to one of the multidimensional outputs of the logic unit.

39. The apparatus claim 38 wherein the parameter determining mechanism is a lookup table mechanism.

40. The apparatus claim 38 wherein the parameter determining mechanism is a set of one or more interpolators.

41. The apparatus claim 38 wherein the combiner unit includes one or more arithmetic units, each arithmetic unit essentially implementing said relationship and having a spectrum input, a multidimensional parameter input, and a spectrum output, the first arithmetic unit's spectrum input coupled to the first memory, the final spectrum output being the output of the combiner unit, and each parameter input coupled to the output of one of the parameter determining mechanisms.

42. The apparatus of claim 41 wherein the number of arithmetic units is the number of colorants.

43. The apparatus claim 41 wherein the logic unit includes one parameter determining mechanism and the combiner unit includes one arithmetic unit whose spectrum input is coupled to the first memory and to the spectrum output of the arithmetic unit, the parameter input of the arithmetic unit coupled to the output of the parameter determining mechanism, whereby the parameter determining mechanism and the arithmetic unit determine the spectrum of each successive colorant sequentially in a number of cycles equal to the number of parameters, and whereby at the end of each cycle the first memory is loaded with the value of the spectrum output of the arithmetic unit.

44. The method of claim 37 further including a color values converter with an input coupled to the output of said combiner unit, additional inputs for specifying illuminant observer values for the conversion of a spectrum to color values in a first color coordinate system, and an output, said output being the color values essentially describing the color appearance of the overprint of the colorants.

45. The method of claim 44 further including a color coordinate converter with an input coupled to the output of the color values converter and an output comprising color coordinates in a second color coordinate system.

46. The method of claim 45 wherein the second color coordinate system is the color coordinate system of a display device.

47. The method of claim 46 wherein the second color coordinate system is the color coordinate system of a printing device.

48. The method of claim 37 wherein, denoting the selected coverage percentage by p, a wavelength by $\lambda$, the spectrum of a p % print of the selected colorant on the base substrate by $R_p(\lambda)$, and the spectrum of the base substrate by $R_{bg}(\lambda)$, said relationship relating $R_p(\lambda)$ to the set of colorant parameters of the selected colorant and to $R_{bg}(\lambda)$ for the case $n_p=2$ is approximately $$R_p(\lambda)=(1-\alpha(p,\lambda))*R_{bg}(\lambda)^{\mu(p\lambda)},$$

and for the case $n_p=3$ is approximately $$R_p(\lambda)=(1-\alpha(p,\lambda))*R_{bg}(\lambda)^{\mu(p,\lambda)}+S(p,\lambda),$$

the set of parameters of the selected colorant including parameters denoted by $\alpha(p,\lambda)$, $\mu(p,\lambda)$ and for the case $n_p=3$, $S(p,\lambda)$.

49. The method of claim 1 wherein the colorant parameters determined in step (b) are substantially independent of the color of the substrate and dependent on the substrate type and the printing technique.

50. The apparatus of claim 37 wherein the colorant parameters are a function of the substrate type the colorant is printed on.

* * * * *